(12) United States Patent
Gaufreteau et al.

(10) Patent No.: US 7,544,683 B2
(45) Date of Patent: Jun. 9, 2009

(54) CYCLOHEXYL DERIVATIVES

(75) Inventors: Delphine Gaufreteau, Bartenheim (FR); Matthias Nettekoven, Grenzach-Wyhlen (DE); Jean-Marc Plancher, Hagenthal-le-Bas (FR); Olivier Roche, Folgensbourg (FR); Sebastien Schmitt, Hagenthal-le-Bas (FR); Tadakatsu Takahashi, Shizuoka (JP)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/136,093

(22) Filed: Jun. 10, 2008

(65) Prior Publication Data

US 2009/0005380 A1 Jan. 1, 2009

(30) Foreign Application Priority Data

Jun. 11, 2007 (EP) .................. 07109945

(51) Int. Cl.
*A61K 31/5377* (2006.01)
*A61K 31/496* (2006.01)
*C07D 295/185* (2006.01)
*C07D 417/12* (2006.01)

(52) U.S. Cl. .............. 514/235.8; 514/252.02; 514/252.11; 514/253.12; 514/254.03; 514/254.05; 514/255.01; 544/121; 544/238; 544/357; 544/360; 544/367; 544/369; 544/372; 544/391

(58) Field of Classification Search ........ None
See application file for complete search history.

(56) References Cited

U.S. PATENT DOCUMENTS

2007/0167436 A1 7/2007 Nettekoven et al.

2007/0173511 A1 7/2007 Nettekoven et al.

FOREIGN PATENT DOCUMENTS

WO WO 2004/101546 11/2004
WO WO 2006/101808 9/2006

OTHER PUBLICATIONS

Masaki et al., *Neuronal Histamine Regulates Food Intake, Adiposity, and Upcoupling Protein Expression in Agouti Yellow ($A^y/a$) Obese Mice*, Endocrinology, 144, pp. 2741-2748 (2003).
Hancock et al., *Antiobesity Effects of A-331440, A Novel Non-Imidazole Histamine $H_3$ Receptor Antagonist*, European Journal of Pharmacology, 487, pp. 183-197 (2004).
Timmerman, H., *Histamine $H_3$ Ligands: Just Pharmacological Tools or Potential therapeutic Agents?*, J. Med. Chem., 33, pp. 4-11 (1990).

Primary Examiner—Emily Bernhardt
(74) *Attorney, Agent, or Firm*—George W. Johnston; Dennis P. Tramaloni; Brian C. Remy

(57) ABSTRACT

The present invention relates to compounds of formula I

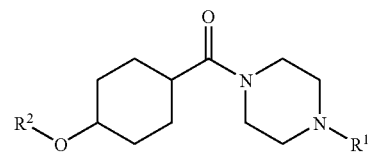

wherein $R^1$ and $R^2$ are as defined in the description and claims, and pharmaceutically acceptable salts thereof. The compounds are useful for the treatment and/or prevention of diseases which are associated with the modulation of H3 receptors.

24 Claims, No Drawings

CYCLOHEXYL DERIVATIVES

PRIORITY TO RELATED APPLICATION(S)

This application claims the benefit of European Patent Application No. 07109945.1, filed Jun. 11, 2007, which is hereby incorporated by reference in its entirety.

BACKGROUND OF THE INVENTION

The present invention is concerned with novel cyclohexyl piperazinyl methanone derivatives, their manufacture, pharmaceutical compositions containing them and their use as medicaments. The active compounds of the present invention are antagonists and/or inverse agonists at the histamine 3 receptor (H3 receptor) and may be useful in treating obesity and other disorders.

Histamine (2-(4-imidazolyl)ethylamine) is one of the aminergic neurotransmitters which is widely distributed throughout the body, for example, in the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11.).

It is therefore an object of the present invention to provide selective, directly acting H3 receptor antagonists and/or inverse agonists.

SUMMARY OF THE INVENTION

The invention is concerned with the compounds of formula I:

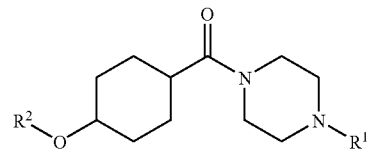

and pharmaceutically acceptable salts and esters thereof, wherein $R^1$ and $R^2$ are as defined in the detailed description and claims. In addition, the present invention relates to the methods of manufacturing and using the compounds of formula I as well as pharmaceutical compositions containing them. The compounds of formula I are antagonists and/or inverse agonists at the histamine 3 receptor (H3 receptor) and are useful as therapeutically active substances, particularly in the treatment and/or prevention of diseases which are associated with the modulation of H3 receptors (such as obesity and other associated disorders).

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms. In preferred embodiments, the alkyl has one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms. In preferred embodiments, the lower alkyl has 1 to 6 carbon atoms and more preferably 1 to 4 carbon atoms. Examples of straight-chain and branched $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred is cyclobutyl.

The term "alkoxy" or "$C_1$-$C_8$-alkoxy" refers to the group R'—O—, wherein R' is lower alkyl and the term "lower alkyl"

has the previously given significance. Examples of lower alkoxy groups are methoxy, ethoxy, n-propoxy, isopropoxy, n-butoxy, isobutoxy, sec-butoxy and tert-butoxy, preferably methoxy and ethoxy and most preferred methoxy.

The term "halogen" refers to fluorine, chlorine, bromine or iodine. In preferred embodiments, the halogen is fluorine, chlorine or bromine.

The term "lower halogenalkyl" or "halogen-$C_1$-$C_8$-alkyl" refers to lower alkyl groups as defined above wherein at least one of the hydrogen atoms of the lower alkyl group is replaced by a halogen atom. In preferred embodiments, the halogen atom is fluoro or chloro, most preferably fluoro. Among the preferred halogenated lower alkyl groups are trifluoromethyl, difluoromethyl, trifluoroethyl, fluoromethyl and chloromethyl, with trifluoromethyl being especially preferred. Similarly, the term "lower hydroxyalkyl" or "hydroxy-$C_1$-$C_8$-alkyl" refers to lower alkyl groups as defined above wherein at least one of the hydrogen atoms of the lower alkyl group is replaced by a hydroxyl group.

The term "lower halogenalkoxy" or "halogen-$C_1$-$C_8$-alkoxy" refers to lower alkoxy groups as defined above wherein at least one of the hydrogen atoms of the lower alkoxy group is replaced by a halogen atom. In preferred embodiments, the halogen atom is fluoro or chloro, most preferably fluoro. Among the preferred halogenated lower alkyl groups are trifluoromethoxy, difluoromethoxy, fluoromethoxy and chloromethoxy, with trifluoromethoxy being especially preferred.

The term "lower alkylsulfonyl" or "$C_1$-$C_8$-alkylsulfonyl" refers to the group —S(O)$_2$—R', wherein R' is a lower alkyl group as defined previously. Examples of lower alkylsulfonyl groups are methylsulfonyl and ethylsulfonyl.

The term "alkylamino" or "$C_1$-$C_8$-alkylamino" refers to the group —NHR', wherein R' is lower alkyl and the term "lower alkyl" has the previously given significance. A preferred alkylamino group is methylamino.

The term "alkylaminocarbonyl" or "$C_1$-$C_8$-alkylaminocarbonyl" refers to the group —C(O)—NHR', wherein R' is lower alkyl and the term "lower alkyl" has the previously given significance. A preferred alkylaminocarbonyl group is methylaminocarbonyl.

The term "dialkylaminocarbonyl" or "di-$C_1$-$C_8$-alkylaminocarbonyl" refers to the group —NR'R", wherein R' and R" are lower alkyl and the term "lower alkyl" has the previously given significance. A preferred dialkylaminocarbonyl group is dimethylaminocarbonyl.

The term "heteroaryl" refers to an aromatic 5- or 6-membered ring comprising one, two, three or four atoms selected from the group consisting of nitrogen, oxygen and sulphur. Examples of heteroaryl groups are furyl, pyridyl, pyrazinyl, pyrimidinyl, pyridazinyl, thienyl, isoxazolyl, thiazolyl, isothiazolyl, thiadiazolyl, oxazolyl, oxadiazolyl, imidazolyl, triazolyl, tetrazolyl and pyrrolyl. Especially preferred are pyridyl, pyrazinyl, pyridazinyl and thiazolyl.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl. Preferred heterocyclyl groups are pyrrolidinyl, imidazolidinyl, oxazolidinyl, piperidinyl and morpholinyl.

The term "oxo" refers to the group =O. Thus, two hydrogen atoms of a carbon atom may be substituted by an oxo group, thus forming a carbonyl (—CO—) group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The salvation can be effected in the course of the manufacturing process or can take place, for example, as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to compounds of formula I:

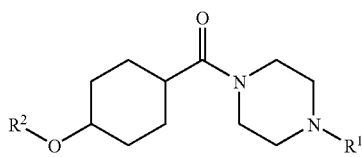

I and pharmaceutically acceptable salts thereof, wherein:
$R^1$ is a $C_1$-$C_8$-alkyl or $C_3$-$C_7$-cycloalkyl; and
$R^2$ is selected from the group consisting of:
(a) phenyl which is substituted by heteroaryl or heterocyclyl, wherein said heteroaryl or heterocyclyl is unsubstituted or substituted with one or two substituents independently selected from the group consisting of:
 (1) $C_1$-$C_8$-alkyl,
 (2) $C_3$-$C_7$-cycloalkyl,
 (3) halogen,
 (4) halogen-$C_1$-$C_8$-alkyl,
 (5) oxo,
 (6) cyano,
 (7) $C_1$-$C_8$-alkoxy,
 (8) halogen-$C_1$-$C_8$-alkoxy, and
 (9) hydroxy-$C_1$-$C_8$-alkyl, and
(b) heteroaryl, wherein the heteroaryl is unsubstituted or substituted with one or two substituents independently selected from the group consisting of:
 (1) $C_1$-$C_8$-alkyl,
 (2) halogen,
 (3) halogen-$C_1$-$C_8$-alkyl,
 (4) cyano,
 (5) $C_1$-$C_8$-alkoxy,
 (6) $C_1$-$C_8$-alkylsulfonyl,
 (7) $C_1$-$C_8$-alkylaminocarbonyl,
 (8) di-$C_1$-$C_8$-alkylaminocarbonyl,
 (9) heterocyclyl which is unsubstituted or substituted with one or two substituents independently selected from the group consisting of $C_1$-$C_8$-alkyl, halogen and oxo, and
 (10) phenyl which is unsubstituted or substituted by one to three substituents independently selected from the group consisting of $C_1$-$C_8$-alkyl, halogen, halogen-$C_1$-$C_8$-alkyl, cyano, and $C_1$-$C_8$-alkoxy.

Preferred compounds of formula I of the present invention are compounds of formula I, wherein $R^1$ is a $C_1$-$C_8$-alkyl, especially isopropyl.

Also preferred are compounds of formula I according to the present invention, wherein $R^1$ is a $C_3$-$C_7$-cycloalkyl, especially cyclobutyl.

Thus, compounds of formula I, wherein $R^1$ is isopropyl or cyclobutyl, are especially preferred.

Furthermore, compounds of formula I according to the present invention are preferred, wherein $R^2$ is phenyl substituted by a heteroaryl or heterocyclyl group, wherein said heteroaryl or heterocyclyl group is unsubstituted or substituted with one or two groups independently selected from the group consisting of: $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy, and hydroxy-$C_1$-$C_8$-alkyl.

Especially preferred are compounds of formula I according to the invention, wherein $R^2$ is phenyl substituted by a heteroaryl or heterocyclyl group selected from the group consisting of: tetrazolyl, triazolyl, oxazolyl, oxadiazolyl, thiazolyl, thiadiazolyl, imidazolyl, pyridinyl, pyrazinyl, piperidinyl, pyrrolidinyl, oxazolidinyl, morpholinyl and imidazolidinyl; wherein said heteroaryl or heterocyclyl group is unsubstituted or substituted with one or two groups independently selected from the group consisting of: $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy and hydroxy-$C_1$-$C_8$-alkyl.

Within this group, compounds of formula I according to the invention are preferred, wherein $R^2$ is phenyl substituted by a heteroaryl group selected from the group consisting of tetrazolyl, triazolyl, oxazolyl, oxadiazolyl, thiazolyl, thiadiazolyl, imidazolyl, pyridinyl and pyrazinyl; said heteroaryl group being unsubstituted or substituted with one or two groups independently selected from the group consisting of: $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy and hydroxy-$C_1$-$C_8$-alkyl.

More preferably, compounds of formula I according to the invention are those, wherein $R^2$ is selected from the group consisting of: [1,2,4]triazol-1-yl, [1,3,4]oxadiazol-2-yl, [1,2,3]thiadiazol-4-yl, imidazol-1-yl, [1,2,4]triazol-1-yl, 5-methyl-[1,3,4]oxadiazol-2-yl, 5-trifluoromethyl-[1,3,4]oxadiazol-2-yl, 5-isopropyl-[1,3,4]oxadiazol-2-yl, 5-cyclopropyl-[1,3,4]oxadiazol-2-yl, 5-tert-butyl-[1,3,4]oxadiazol-2-yl, [1,2,4]oxadiazol-3-yl, 5-methyl-[1,2,4]oxadiazol-3-yl, [1,2,4]oxadiazol-5-yl, 3-methyl-[1,2,4]oxadiazol-5-yl, thiazol-2-yl, pyridin-2-yl, pyridin-3-yl, pyridin-4-yl, pyrazin-2-yl, oxazol-2-yl and tetrazol-5-yl.

Further preferred compounds of formula I according to the invention are those, wherein $R^2$ is phenyl substituted by a heterocyclyl group selected from the group consisting of: piperidinyl, pyrrolidinyl, oxazolidinyl, morpholinyl and imidazolidinyl; said heterocyclyl group being unsubstituted or substituted with one or two groups independently selected from the group consisting of: $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy and hydroxy-$C_1$-$C_8$-alkyl.

Especially preferred are compounds of formula I, wherein $R^2$ is phenyl substituted by a heterocyclyl group selected from the group consisting of: 2-oxo-piperidin-1-yl, 2-oxo-pyrrolidin-1-yl, 2-oxo-oxazolidin-3-yl, 3-oxo-morpholin-4-yl and 3-methyl-2-oxo-imidazolidin-1-yl.

Also preferred are compounds of formula I according to the present invention, wherein $R^2$ is heteroaryl, wherein the heteroaryl ring is unsubstituted or substituted with one or two groups independently selected from the group consisting of: $C_1$-$C_8$-alkyl; halogen; halogen-$C_1$-$C_8$-alkyl; cyano; $C_1$-$C_8$-alkoxy, $C_1$-$C_8$-alkylsulfonyl; $C_1$-$C_8$-alkylaminocarbonyl; di-$C_1$-$C_8$-alkylaminocarbonyl; heterocyclyl which is unsubstituted or substituted with one or two groups independently selected from the group consisting of $C_1$-$C_8$-alkyl, halogen and oxo; and phenyl which is unsubstituted or substituted by one to three groups selected from the group consisting of: $C_1$-$C_8$-alkyl, halogen, halogen-$C_1$-$C_8$-alkyl, cyano, and $C_1$-$C_8$-alkoxy.

Within this group, compounds of formula I according to the invention are preferred, wherein $R^2$ is heteroaryl selected from the group consisting of: pyridyl, pyridazinyl and thiazolyl, said heteroaryl ring being unsubstituted or substituted with one or two groups independently selected from the group consisting of: $C_1$-$C_8$-alkyl; halogen; halogen-$C_1$-$C_8$-alkyl; cyano; $C_1$-$C_8$-alkoxy, $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two groups independently selected from $C_1$-$C_8$-alkyl, halogen and oxo; and phenyl which is unsubstituted or substituted by one to three groups selected from $C_1$-$C_8$-alkyl, halogen, halogen-$C_1$-$C_8$-alkyl, cyano, and $C_1$-$C_8$-alkoxy.

Especially preferred are compounds of formula I according to the invention, wherein $R^2$ is pyridyl or pyridazinyl, said pyridyl or pyridazinyl ring being unsubstituted or substituted with one or two groups independently selected from the group consisting of: $C_1$-$C_8$-alkyl; halogen; halogen-$C_1$-$C_8$-alkyl; cyano; $C_1$-$C_8$-alkoxy; $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two groups independently selected from $C_1$-$C_8$-alkyl, halogen and oxo; and phenyl which is unsubstituted or substituted by one to three groups selected from the group consisting of $C_1$-$C_8$-alkyl, halogen, halogen-$C_1$-$C_8$-alkyl, cyano, and $C_1$-$C_8$-alkoxy.

Also especially preferred are compounds of formula I, wherein $R^2$ is thiazolyl, said thiazolyl ring being unsubstituted or substituted with one or two groups independently selected from the group consisting of: $C_1$-$C_8$-alkyl; halogen; halogen-$C_1$-$C_8$-alkyl; cyano; $C_1$-$C_8$-alkoxy, $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two groups independently selected from $C_1$-$C_8$-alkyl, halogen and oxo; and phenyl which is unsubstituted or substituted by one to three groups selected from the group consisting of: $C_1$-$C_8$-alkyl, halogen, halogen-$C_1$-$C_8$-alkyl, cyano, and $C_1$-$C_8$-alkoxy.

More preferably, compounds of formula I according to the invention are those, wherein $R^2$ is selected from the group consisting of: 6-chloro-pyridin-3-yl, 6-bromo-pyridin-3-yl, 6-cyano-pyridin-3-yl, 6-trifluoromethyl-pyridin-3-yl, 5-fluoro-pyridin-3-yl, 5-bromo-pyridin-2-yl, 5-chloro-pyridin-2-yl, 5-trifluoromethyl-pyridin-2-yl, 3-chloro-5-trifluoromethyl-pyridin-2-yl, 3-fluoro-5-trifluormethyl-pyridin-2-yl, 5-cyano-pyridin-2-yl, 5-methylsulfonyl-pyridin-2-yl, 5-methylaminocarbonyl-pyridin-2-yl, 5-dimethylaminocarbonyl-pyridin-2-yl, 5-(2-oxo-pyrrolidin-1-yl)-pyridin-2-yl, 6-iodo-pyridazin-3-yl and 6-(2-oxo-pyrrolidin-1-yl)-pyridazin-3-yl.

Furthermore, compounds of formula I according to the present invention are preferred, wherein $R^2$ and the piperazinyl-carboxy group are in trans-configuration, i.e. compounds of formula I having the formula Ia:

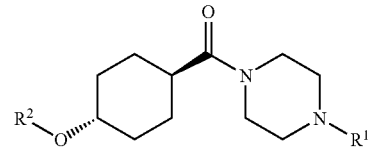

Preferred compounds of formula I of the present invention are the following:
trans-(4-cyclobutyl-piperazin-1-yl)-[4-(4-[1,2,4]triazol-1-yl-phenoxy)-cyclohexyl]-methanone,
trans-[4-(6-chloro-pyridin-3-yloxy)-cyclohexyl]-(4-cyclobutyl-piperazin-1-yl)-methanone,
trans-[4-(5-chloro-pyridin-2-yloxy)-cyclohexyl]-(4-cyclobutyl-piperazin-1-yl)-methanone,
cis-[4-(6-chloro-pyridin-3-yloxy)-cyclohexyl]-(4-cyclobutyl-piperazin-1-yl)-methanone,
cis-[4-(5-chloro-pyridin-2-yloxy)-cyclohexyl]-(4-cyclobutyl-piperazin-1-yl)-methanone,
trans-(4-isopropyl-piperazin-1-yl)-[4-(4-[1,3,4]oxadiazol-2-yl-phenoxy)-cyclohexyl]-methanone,
trans-(4-isopropyl-piperazin-1-yl)-[4-(4-[1,2,3]thiadiazol-4-yl-phenoxy)-cyclohexyl]-methanone,
trans-[4-(4-imidazol-1-yl-phenoxy)-cyclohexyl]-(4-isopropyl-piperazin-1-yl)-methanone,
trans-(4-isopropyl-piperazin-1-yl)-[4-(4-[1,2,4]triazol-1-yl-phenoxy)-cyclohexyl]-methanone,
trans-6-[4-(4-cyclobutyl-piperazine-1-carbonyl)-cyclohexyloxy]-nicotinonitrile,
trans-6-[4-(4-isopropyl-piperazine-1-carbonyl)-cyclohexyloxy]-nicotinonitrile,
trans-(4-isopropyl-piperazin-1-yl)-[4-(5-methanesulfonyl-pyridin-2-yloxy)-cyclohexyl]-methanone,
trans-(4-cyclobutyl-piperazin-1-yl)-[4-(5-methanesulfonyl-pyridin-2-yloxy)-cyclohexyl]-methanone,
trans-6-[4-(4-cyclobutyl-piperazine-1-carbonyl)-cyclohexyloxy]-N-methyl-nicotinamide,
trans-6-[4-(4-cyclobutyl-piperazine-1-carbonyl)-cyclohexyloxy]-N,N-dimethyl-nicotinamide,
trans-[4-(5-chloro-pyridin-2-yloxy)-cyclohexyl]-(4-isopropyl-piperazin-1-yl)-methanone,
trans-[4-(6-iodo-pyridazin-3-yloxy)-cyclohexyl]-(4-isopropyl-piperazin-1-yl)-methanone,
trans-[4-(5-bromo-pyridin-2-yloxy)-cyclohexyl]-(4-isopropyl-piperazin-1-yl)-methanone,
trans-5-[4-(4-cyclobutyl-piperazine-1-carbonyl)-cyclohexyloxy]-pyridine-2-carbonitrile,
trans-[4-(6-bromo-pyridin-3-yloxy)-cyclohexyl]-(4-cyclobutyl-piperazin-1-yl)-methanone,
trans-(4-cyclobutyl-piperazin-1-yl)-[4-(5-fluoro-pyridin-3-yloxy)-cyclohexyl]-methanone,
trans-5-[4-(4-isopropyl-piperazine-1-carbonyl)-cyclohexyloxy]-pyridine-2-carbonitrile,
trans-(4-isopropyl-piperazin-1-yl)-[4-(6-trifluoromethyl-pyridin-3-yloxy)-cyclohexyl]-methanone,
trans-(4-isopropyl-piperazin-1-yl)-[4-(5-trifluoromethyl-pyridin-2-yloxy)-cyclohexyl]-methanone,
trans-[4-(3-chloro-5-trifluoromethyl-pyridin-2-yloxy)-cyclohexyl]-(4-isopropyl-piperazin-1-yl)-methanone,
trans-[4-(3-fluoro-5-trifluoromethyl-pyridin-2-yloxy)-cyclohexyl]-(4-isopropyl-piperazin-1-yl)-methanone,
trans-2-[4-(4-isopropyl-piperazine-1-carbonyl)-cyclohexyloxy]-thiazole-4-carboxylic acid methylamide, trans-(4-isopropyl-piperazin-1-yl)-{4-[4-(5-methyl-[1,3,4]
oxadiazol-2-yl)-phenoxy]-cyclohexyl}-methanone,
trans-(4-cyclobutyl-piperazin-1-yl)-{4-[4-(5-methyl-[1,3,4]
oxadiazol-2-yl)-phenoxy]-cyclohexyl}-methanone,
trans-(4-isopropyl-piperazin-1-yl)-{4-[4-(5-trifluoromethyl-
[1,3,4]oxadiazol-2-yl)-phenoxy]-cyclohexyl}-methanone,
trans-{4-[4-(5-isopropyl-[1,3,4]oxadiazol-2-yl)-phenoxy]-
cyclohexyl}-(4-isopropyl-piperazin-1-yl)-methanone,
trans-{4-[4-(5-cyclopropyl-[1,3,4]oxadiazol-2-yl)-phenoxy]-cyclohexyl}-(4-isopropyl-piperazin-1-yl)-methanone,
trans-{4-[4-(5-tert-butyl-[1,3,4]oxadiazol-2-yl)-phenoxy]-
cyclohexyl}-(4-isopropyl-piperazin-1-yl)-methanone,
trans-(4-isopropyl-piperazin-1-yl)-{4-[4-(5-methyl-[1,2,4]
oxadiazol-3-yl)-phenoxy]-cyclohexyl}-methanone,
trans-(4-cyclobutyl-piperazin-1-yl)-{4-[4-(5-methyl-[1,2,4]
oxadiazol-3-yl)-phenoxy]-cyclohexyl}-methanone,
trans-(4-isopropyl-piperazin-1-yl)-{4-[4-(3-methyl-[1,2,4]
oxadiazol-5-yl)-phenoxy]-cyclohexyl}-methanone,
trans-1-{4-[4-(4-isopropyl-piperazine-1-carbonyl)-cyclo-
hexyloxy]-phenyl}-piperidin-2-one,
trans-1-{4-[4-(4-cyclobutyl-piperazine-1-carbonyl)-cyclo-
hexyloxy]-phenyl}-pyrrolidin-2-one,
trans-3-{4-[4-(4-cyclobutyl-piperazine-1-carbonyl)-cyclo-
hexyloxy]-phenyl}-oxazolidin-2-one,
trans-3-{4-[4-(4-isopropyl-piperazine-1-carbonyl)-cyclo-
hexyloxy]-phenyl}-oxazolidin-2-one,
trans-4-{4-[4-(4-isopropyl-piperazine-1-carbonyl)-cyclo-
hexyloxy]-phenyl}-morpholin-3-one,
trans-4-{4-[4-(4-cyclobutyl-piperazine-1-carbonyl)-cyclo-
hexyloxy]-phenyl}-morpholin-3-one,
trans-1-{4-[4-(4-isopropyl-piperazine-1-carbonyl)-cyclo-
hexyloxy]-phenyl}-3-methyl-imidazolidin-2-one,
trans-1-{4-[4-(4-isopropyl-piperazine-1-carbonyl)-cyclo-
hexyloxy]-phenyl}-pyrrolidin-2-one,
trans-1-{6-[4-(4-isopropyl-piperazine-1-carbonyl)-cyclo-
hexyloxy]-pyridin-3-yl}-pyrrolidin-2-one,
trans-1-{6-[4-(4-isopropyl-piperazine-1-carbonyl)-cyclo-
hexyloxy]-pyridazin-3-yl}-pyrrolidin-2-one,
trans-(4-isopropyl-piperazin-1-yl)-[4-(4-thiazol-2-yl-phe-
noxy)-cyclohexyl]-methanone,
trans-(4-isopropyl-piperazin-1-yl)-[4-(4-pyridin-2-yl-phe-
noxy)-cyclohexyl]-methanone,
trans-(4-isopropyl-piperazin-1-yl)-[4-(4-pyridin-3-yl-phe-
noxy)-cyclohexyl]-methanone,
trans-(4-isopropyl-piperazin-1-yl)-[4-(4-pyridin-4-yl-phe-
noxy)-cyclohexyl]-methanone,
trans-(4-isopropyl-piperazin-1-yl)-[4-(4-pyrazin-2-yl-phe-
noxy)-cyclohexyl]-methanone,
trans-(4-isopropyl-piperazin-1-yl)-[4-(4-oxazol-2-yl-phe-
noxy)-cyclohexyl]-methanone,
{4-[5-(3,4-difluoro-phenyl)-pyridin-2-yloxy]-cyclohexyl}-
(4-isopropyl-piperazin-1-yl)-methanone,
(4-isopropyl-piperazin-1-yl)-{4-[4-(1H-tetrazol-5-yl)-phe-
noxy]-cyclohexyl}-methanone, and pharmaceutically acceptable salts thereof.
Especially preferred are the following compounds:
trans-(4-cyclobutyl-piperazin-1-yl)-[4-(4-[1,2,4]triazol-1-
yl-phenoxy)-cyclohexyl]-methanone,
trans-(4-isopropyl-piperazin-1-yl)-{4-[4-(5-methyl-[1,3,4]
oxadiazol-2-yl)-phenoxy]-cyclohexyl}-methanone,
trans-(4-cyclobutyl-piperazin-1-yl)-{4-[4-(5-methyl-[1,3,4]
oxadiazol-2-yl)-phenoxy]-cyclohexyl}-methanone,
trans-{4-[4-(5-isopropyl-[1,3,4]oxadiazol-2-yl)-phenoxy]-
cyclohexyl}-(4-isopropyl-piperazin-1-yl)-methanone,
trans-{4-[4-(5-cyclopropyl-[1,3,4]oxadiazol-2-yl)-phe-
noxy]-cyclohexyl}-(4-isopropyl-piperazin-1-yl)-metha-
none,
trans-{4-[4-(5-tert-butyl-[1,3,4]oxadiazol-2-yl)-phenoxy]-
cyclohexyl}-(4-isopropyl-piperazin-1-yl)-methanone,
trans-(4-isopropyl-piperazin-1-yl)-{4-[4-(3-methyl-[1,2,4]
oxadiazol-5-yl)-phenoxy]-cyclohexyl}-methanone,
trans-4-{4-[4-(4-cyclobutyl-piperazine-1-carbonyl)-cyclo-
hexyloxy]-phenyl}-morpholin-3-one,
trans-1-{4-[4-(4-isopropyl-piperazine-1-carbonyl)-cyclo-
hexyloxy]-phenyl}-3-methyl-imidazolidin-2-one,
trans-(4-isopropyl-piperazin-1-yl)-[4-(4-thiazol-2-yl-phe-
noxy)-cyclohexyl]-methanone,
trans-(4-isopropyl-piperazin-1-yl)-[4-(4-pyridin-3-yl-phe-
noxy)-cyclohexyl]-methanone,
trans-(4-isopropyl-piperazin-1-yl)-[4-(4-pyridin-4-yl-phe-
noxy)-cyclohexyl]-methanone,
trans-(4-isopropyl-piperazin-1-yl)-[4-(4-pyrazin-2-yl-phe-
noxy)-cyclohexyl]-methanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of the formula II

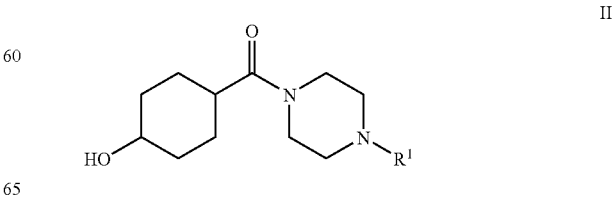

wherein $R^1$ is as defined herein before, with an alcohol of the formula III

    III wherein $R^2$ is as defined herein before, in the presence of a trialkylphosphine or triphenylphosphine and of a dialkyl azodicarboxylate to obtain a compound of the formula I

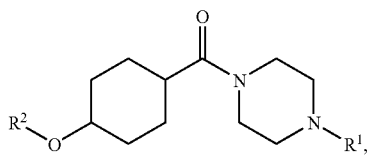    I wherein $R^1$ and $R^2$ are as defined herein before, and optionally, converting the compound obtained into a pharmaceutically acceptable acid addition salt, or, alternatively, b) reacting a compound of the formula

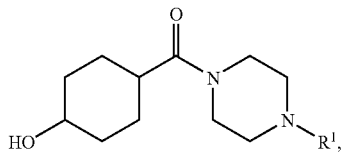    II wherein $R^1$ is as defined herein before, with a compound of the formula IV

    IV wherein $R^2$ is as defined herein before and X is a group selected from halogen, nitro, methane sulfonyloxy, toluene sulfonyloxy and trifluoromethane sulfonyloxy, in the presence of a base to obtain a compound of the formula I

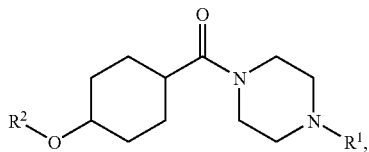    I wherein $R^1$ and $R^2$ are as defined herein before, and, optionally, converting the compound of formula I into a pharmaceutically acceptable acid addition salt.

The preparation of compounds of formula I of the present invention may be carried out in sequential or convergent synthetic routes. Syntheses of the invention are shown in the following scheme. The skills required for carrying out the reaction and purification of the resulting products are known to those skilled in the art. The substituents and indices used in the following description of the processes have the significance given herein before unless indicated to the contrary. In more detail, the compounds of formula I can be manufactured by the methods given below, by the methods given in the examples or by analogous methods. Appropriate reaction conditions for the individual reaction steps are known to a person skilled in the art.

Starting materials are either commercially available or can be prepared by methods analogous to the methods given below, by methods described in references cited in the description or in the examples, or by methods known in the art.

In the Scheme 1 below, 4-hydroxycyclohexanecarboxylic acid (1) (cis or trans) is commercially available and may be reacted with the compound of general formula (2) in the presence of a coupling reagent and a base to give a compound of general formula (3) (step 1). Suitable coupling (reducing) agents for use in step 1 include 1-[bis(dimethyl-amino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU), and the like, more preferably TBTU. Suitable bases for use in the above step 1 include triethylamine, N,N-diisopropylethylamine (DIPEA), pyridine, 2,6-lutidine, 2,4,6-collidine, N,N-dimethylaminopyridine, N-methylmorpholine, and the like, more preferably DIPEA. Suitable solvents for use in the above step 1 include dimethylformamide (DMF), dimethylacetamide (DMA), tetrahydrofurane (THF), dioxane, dichloromethane, 1,2-dichloroethane, and the like, more preferably DMF. The reaction temperature of the above step 1 is in the range from –20° C. to 100° C., preferably from –20° C. to 40° C., though it is not specifically limited so far as the reaction proceeds.

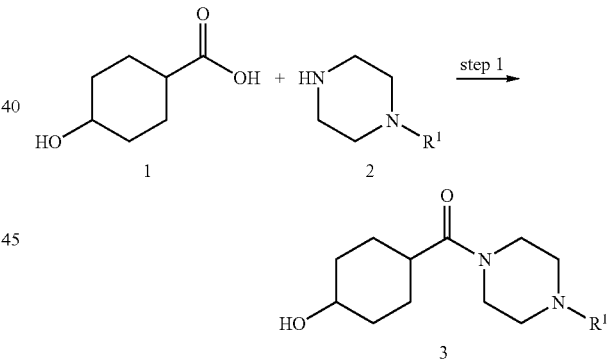

In Scheme 2, the compound of general formula (3) may be reacted with the compound of general formula (4) (A=an optionally substituted aryl or heteroaryl group) in the presence of a trialkylphosphine or triphenylphosphine and a dialkyl azodicarboxylate to give a compound of general formula (5) (step 2). Suitable dialkyl azodicarboxylates for use in step 2 include di-tert-butyl azodicarboxylate, diethyl azodicarboxylate, and the like, more preferably di-tert-butyl azodicarboxylate. Suitable solvents for use in step 2 include benzene, toluene, diethyl ether, THF, dioxane, t-butyl methyl ether, dichloromethane, 1,2-dichloroethane, and the like more preferably THF. The reaction temperature of the above step 1 is in the range from –40° C. to 100° C., preferably from –20° C. to 50° C., though it is not specifically limited so far as the reaction proceeds.

Scheme 2

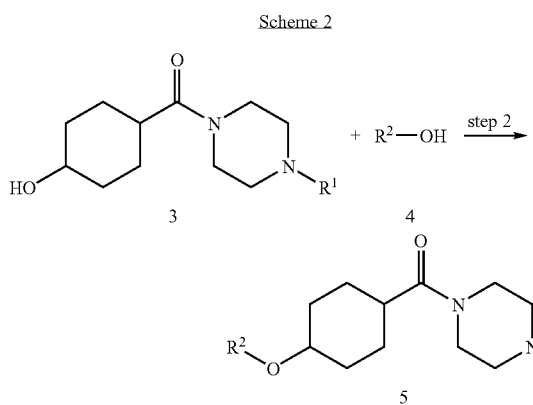

In Scheme 3, the compound of general formula (3) may be reacted with the compound of general formula (6) (A=an optionally substituted aryl or heteroaryl group, X=a halogen group, a nitro group, a methane sulfonyloxy group, a toluene sulfonyloxy group, a trifluoromethane sulfonyloxy group) in the presence of a base to give a compound of general formula (5) (step 3). Suitable bases for use in step 3 include sodium tert-butoxide, potassium tert-butoxide, n-butyl lithium, sec-butyl lithium, tert-butyl lithium, lithium diisopropylamide, lithium dicyclohexylamide, lithium bis(trimethylsilyl)amide, potassium bis(trimethylsilyl)amide, sodium hydride, potassium hydride, potassium carbonate, sodium carbonate, cesium carbonate, sodium hydrogencarbonate and the like, more preferably sodium hydride. Suitable solvents for use in the above step 3 include benzene, toluene, diethyl ether, THF, dioxane, t-butyl methyl ether, DMF, DMA, and the like, the mixture, more preferably DMA and DMA-TI-IF. The reaction temperature of the above step 3 is in the range from −40° C. to 300° C., preferably from 0° C. to 250° C., though it is not specifically limited so far as the reaction proceeds.

Scheme 3

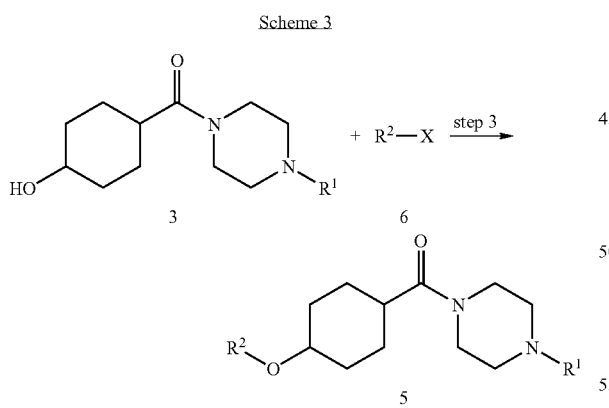

In Scheme 4, the compound of general formula (7) (A is an optionally substituted aryl or heteroaryl group, R' is an alkyl group) may hydrolyzed in the presence of a base to give a compound of general formula (8) (step 4). Suitable bases for use in step 3 include sodium hydroxide, potassium hydroxide, lithium hydroxide, potassium carbonate, sodium carbonate, cesium carbonate, sodium hydrogencarbonate and the like, more preferably lithium hydroxide. Suitable solvents for use in step 4 include methanol, ethanol, THF, dioxane, 1,2-dimethoxyethane, water and the like, the mixture, more preferably methanol-water-THF. The reaction temperature of the above step 4 is in the range from −10° C. to 150° C., preferably from 0° C. to 100° C., though it is not specifically limited so far as the reaction proceeds.

Scheme 4

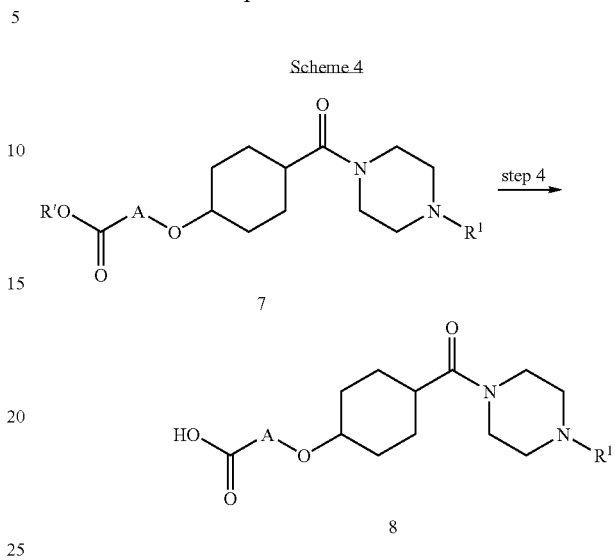

In Scheme 5, the compound of general formula (8) (A is an optionally substituted aryl or heteroaryl group) may reacted with tert-butyl carbamate in the presence of a coupling reagent and a base to give a compound of general formula (9) (step 5). Suitable coupling reagents for use in the above step 5 include TBTU, HATU, HOBT, and the like, more preferably HOBT. Suitable bases for use in the above step 5 include triethylamine, N,N-diisopropylethylamine (DIPEA), pyridine, 2,6-lutidine, 2,4,6-collidine, N,N-dimethylaminopyridine, N-methylmorpholine, and the like, more preferably N-methylmorpholine. Suitable solvents for use in the above step 5 include DMF, DMA, THF, dioxane, dichloromethane, 1,2-dichloroethane, and the like more preferably dichloromethane. The reaction temperature of the above step 5 is in the range from −20° C. to 100° C., preferably from 0° C. to 40° C., though it is not specifically limited so far as the reaction proceeds.

Scheme 5

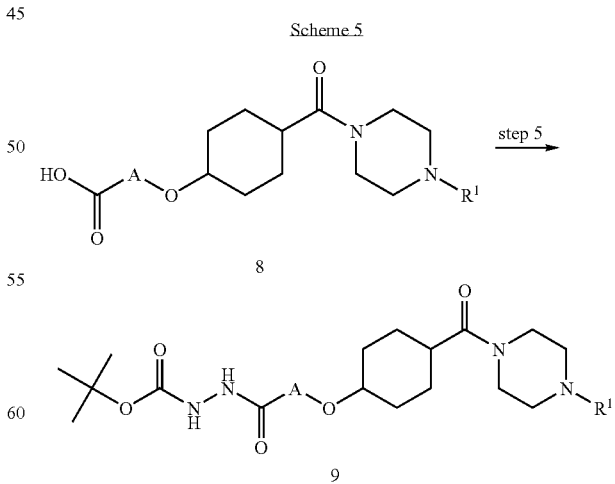

In Scheme 6, the compound of general formula (9) (A=an optionally substituted aryl or heteroaryl group) may be deprotected in the presence of an acid to give a compound of general formula (10) (step 6). Suitable acids for use in step 6 include hydrochloric acid, sulfuric acid, acetic acid, trifluoroacetic acid, methane sulfonic acid, trifluoromethane sulfonic acid, and the like, more preferably hydrochloric acid. Suitable solvents for use in step 6 include DMF, DMA, THF, dioxane, dichloromethane, 1,2-dichloroethane, methanol, ethanol, 1,2-dimethoxyethane, water, benzene, toluene and the like, more preferably dichloromethane. The reaction temperature of the above step 6 is in the range from −20° C. to 150° C., preferably from 0° C. to 100° C., though it is not specifically limited so far as the reaction proceeds.

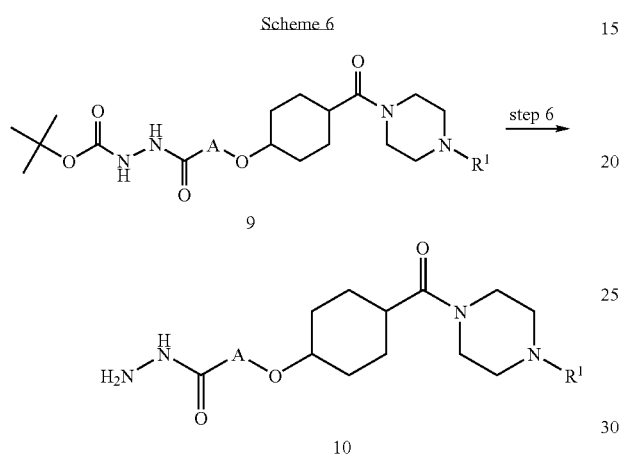

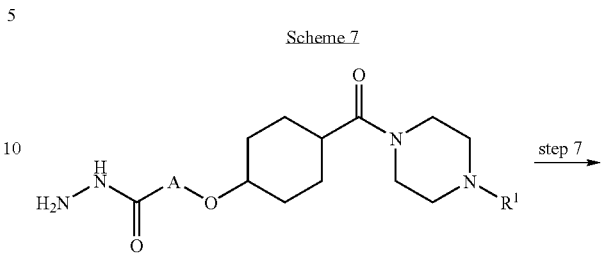

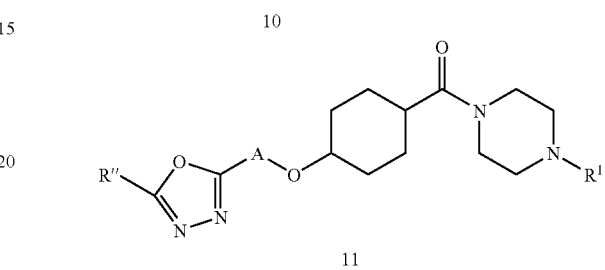

In Scheme 7, the compound of general formula (10) (A is an optionally substituted aryl or heteroaryl group) may be reacted with an orthoester to give a compound of general formula (11) (R" is an optionally substituted alkyl group) (step 7). The reaction temperature of step 7 is in the range from 0° C. to 200° C., preferably from 20° C. to 150° C., though it is not specifically limited so far as the reaction proceeds.

In addition, the compound of general formula (10) (A is an optionally substituted aryl or heteroaryl group) may be reacted with a carboxylic acid anhydride in the presence of a base, followed by a treatment with thionyl chloride to give a compound of general formula (11) (R" is an optionally substituted alkyl group) (step 7). In this case, suitable bases for use in the above step 7 include triethylamine, N,N-diisopropylethylamine (DIPEA), pyridine, 2,6-lutidine, 2,4,6-collidine, N,N-dimethylaminopyridine, N-methylmorpholine, and the like, more preferably triethylamine. In this case, suitable solvents for use in the above step 7 include THF, dioxane, dichloromethane, 1,2-dichloroethane, and the like more preferably dichloromethane. The reaction temperature of the above step 7 is in the range from −20° C. to 100° C., preferably from 0° C. to 100° C., though it is not specifically limited so far as the reaction proceeds.

In addition, the compound of general formula (10) (A is an optionally substituted aryl or heteroaryl group) may be reacted with a carboxylic acid in the presence of phosphorus oxychloride to give a compound of general formula (11) (R" is an optionally substituted alkyl group) (step 7). The reaction temperature of step 7 is in the range from −20° C. to 150° C., preferably from 20° C. to 150° C., though it is not specifically limited so far as the reaction proceeds.

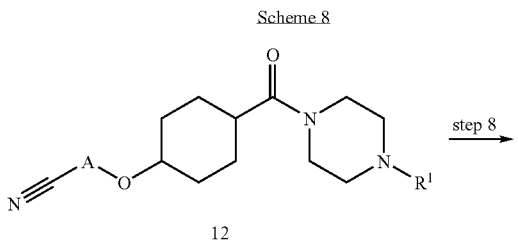

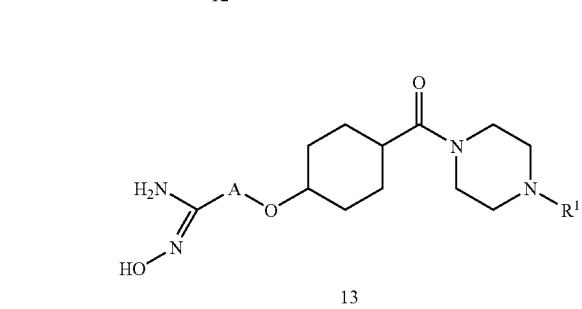

In Scheme 8, the compound of general formula (12) (A is an optionally substituted aryl or heteroaryl group) may be reacted with hydroxylamine hydrochloride in the presence of a base to give a compound of general formula (13) (step 8). Suitable bases for use in step 8 include triethylamine, N,N-diisopropylethylamine (DIPEA), pyridine, 2,6-lutidine, 2,4,6-collidine, N,N-dimethylaminopyridine, N-methylmorpholine, and the like, more preferably triethylamine. Suitable solvents for use in step 8 include THF, dioxane, dichloromethane, 1,2-dichloroethane, methanol, ethanol, 1,2-dimethoxyethane and the like, more preferably ethanol. The reaction temperature of step 8 is in the range from 20° C. to 200° C., preferably from 20° C. to 100° C., though it is not specifically limited so far as the reaction proceeds.

Scheme 9

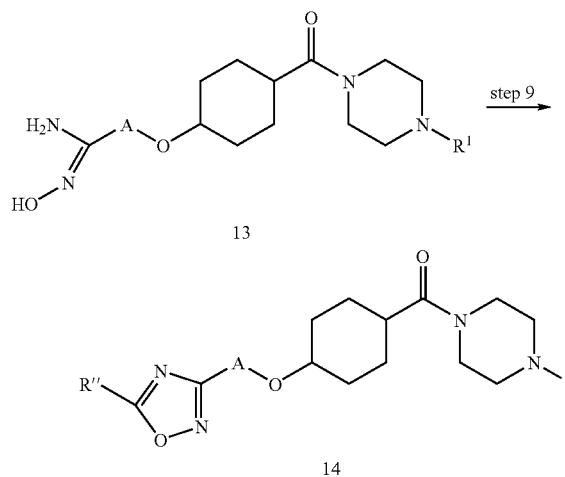

In the above scheme, the compound of general formula (13) (A is an optionally substituted aryl or heteroaryl group) may be reacted with an ester in the presence of a base to give a compound of general formula (14) (R" is an optionally substituted alkyl group) (step 9). Suitable bases for use in step 9 include sodium tert-butoxide, potassium tert-butoxide, sodium hydride, potassium hydride, potassium carbonate, sodium carbonate, cesium carbonate, sodium hydrogencarbonate and the like, more preferably sodium hydride. Suitable solvents for use in step 9 include THF, dioxane, 1,2-dimethoxyethane and the like, more preferably THF. The reaction temperature of the above step 9 is in the range from 0° C. to 150° C., preferably from 20° C. to 100° C., though it is not specifically limited so far as the reaction proceeds.

Scheme 10

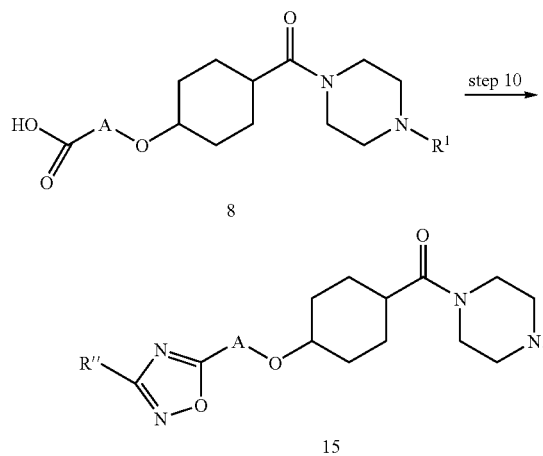

In Scheme 10, the compound of general formula (8) (A is an optionally substituted aryl or heteroaryl group) may be reacted with 1,1'-carbonyl-diimidazole, followed by a treatment with an N-hydroxy alkylamidine and a base to give a compound of general formula (15) (R" is an optionally substituted alkyl group) (step 10). Suitable bases for use in step 10 include sodium hydride, potassium hydride, potassium carbonate, sodium carbonate, cesium carbonate, sodium hydrogencarbonate and the like, more preferably sodium hydride. Suitable solvents for use in step 10 include THF, dioxane, 1,2-dimethoxyethane and the like, more preferably THF. The reaction temperature of the above step 10 is in the range from 0° C. to 150° C., preferably from 20° C. to 100° C., though it is not specifically limited so far as the reaction proceeds.

Scheme 11

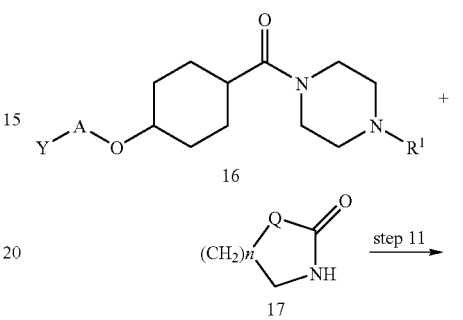

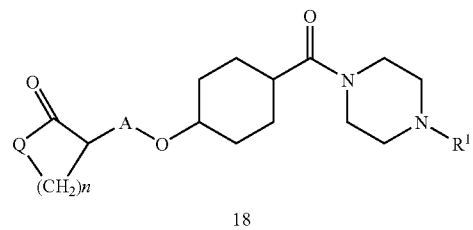

In the Scheme 11, the compound of general formula (16) (A is an optionally substituted aryl or heteroaryl group, Y is a halogen group, a trifluoromethane sulfonyloxy group) may be reacted with the compound of general formula (17) (Q is $CH_2$, O, N—$R^3$, n is 0 to 3, $R^3$ is hydrogen or a lower alkyl group) in the presence of cupper and a base to give a compound of general formula (18) (step 11). Suitable bases for use in step 11 include potassium carbonate, sodium carbonate, cesium carbonate, sodium hydrogencarbonate and the like, more preferably potassium carbonate. The reaction temperature of the above step 11 is in the range from 0° C. to 250° C., preferably from 20° C. to 200° C., though it is not specifically limited so far as the reaction proceeds.

Scheme 12

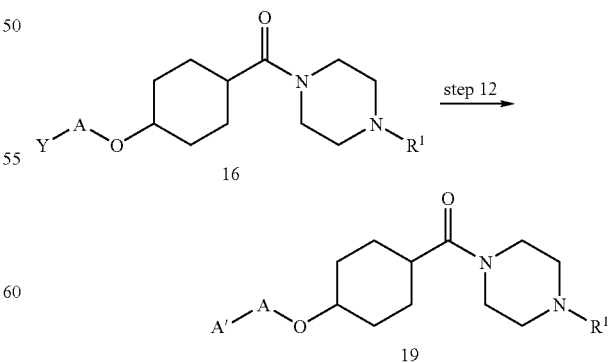

In the above scheme, the compound of general formula (16) (A is an optionally substituted aryl or heteroaryl group, Y is a halogen group, a trifluoromethane sulfonyloxy group)

may reacted with an arylstannane or a hetarylstannane in the presence of palladium catalyst to give a compound of general formula (19) (A' is an optionally substituted aryl or heteroaryl group) (step 12). Suitable palladium catalysts for use in step 12 include bis(triphenylphosphine)palladium(II) dichloride, tetrakis(triphenyl-phosphine)palladium, Pd(dba)$_2$, Pd$_2$(dba)$_2$-CHCl$_3$, palladium acetate, palladium chloride, [1,1'-bis(diphenylphosphino)ferrocene]palladium chloride, and the like, more preferably bis(triphenylphosphine)palladium(II) dichloride. Suitable solvents for use in step 12 include DMF, DMA, 1,3-dimethyl-2-imidazolidinone, THF, dioxane, 1,2-dimethoxyethane, toluene, acetonitrile and the like, more preferably THF. The reaction temperature of the above step 12 is in the range from 0° C. to 200° C., preferably from 20° C. to 150° C., though it is not specifically limited so far as the reaction proceeds.

In addition, the compound of general formula (16) (A is an optionally substituted aryl or heteroaryl group, Y is a halogen group, a trifluoromethane sulfonyloxy group) may reacted with an arylboronic acid, a heteroarylboronic acid, an arylboronic acid ester, or a heteroarylboronic acid ester in the presence of palladium catalyst and a base to give a compound of general formula (19) (A' is an optionally substituted aryl or heteroaryl group) (step 12). In this case, suitable palladium catalysts for use in step 12 include bis(triphenylphosphine)palladium(II) dichloride, tetrakis(triphenylphosphine)palladium, Pd(dba)$_2$, Pd2(dba)$_2$-CHCl$_3$, palladium acetate, palladium chloride, [1,1'-bis(diphenyl-phosphino)ferrocene]palladium chloride, and the like, more preferably tetrakis-(triphenylphosphine)palladium. In this case, suitable bases for use in step 12 include potassium carbonate, sodium carbonate, cesium carbonate, sodium hydrogencarbonate and the like, more preferably sodium carbonate. In this case, suitable solvents for use in step 12 include DMF, DMA, 1,3-dimethyl-2-imidazolidinone, THF, dioxane, 1,2-dimethoxyethane, toluene, acetonitrile, water and the like, the mixture, more preferably toluene-water. In this case, the reaction temperature of the above step 12 is in the range from 0° C. to 200° C., preferably from 20° C. to 150° C., though it is not specifically limited so far as the reaction proceeds.

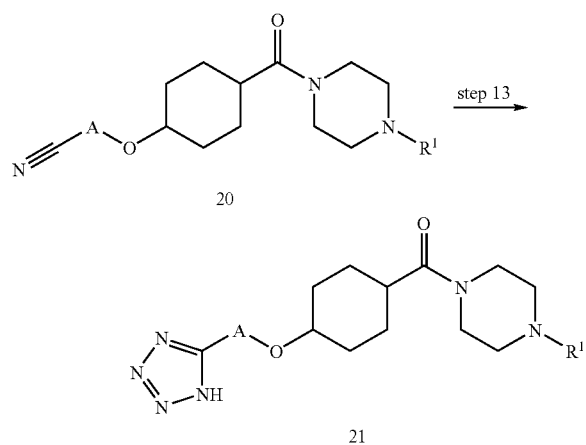

In Scheme 13, the compound of general formula (20) (A is an optionally substituted aryl or heteroaryl group) may be reacted with a sodium azide, combination of sodium azide and triethylamine hydrochloride, azidotributyltin or a combination of trimethylsilylazide and di-n-butyltin oxide to give a compound of general formula 21) (A is an optionally substituted aryl or heteroaryl group) (step 13). Suitable solvents for use in step 13 include THF, dioxane, 1,2-dimethoxyethane, toluene and the like, more preferably toluene. The reaction temperature of the above step 13 is in the range from 0° C. to 200° C., preferably from 20° C. to 150° C., though it is not specifically limited so far as the reaction proceeds.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a pharmaceutical composition for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a pharmaceutical composition for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a pharmaceutical composition for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a pharmaceutical composition for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazein (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an object of the invention is the method as described above for the simultaneous, separate or sequential administration of a compound according to formula I and a therapeutically effective amount of an anti-hypertensive agent.

The use of a compound of formula I in the manufacture of a pharmaceutical composition for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM MgCl$_2$× 6H$_2$O pH 7.4. Washing Buffer: 50 mM Tris-HCl pH 7.4 and 5 mM MgCl$_2$×6H$_2$O and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R-CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-methylhistamine dihydrobromide.

All compounds were tested at a single concentration in duplicate. Compounds that showed an inhibition of [$^3$H]-RAMH by more than 50% were tested again to determine IC$_{50}$ in a serial dilution experiment, meaning concentrations were spanning 10 points starting from 4.6×10$^{-6}$ M to 1.0× 10$^{-9}$ M. The dilution factor was 1/2.15 for the whole series. The concentration at which 50% inhibition of the radioligand $^3$H(R)α-methylhistamine is obtained (the IC$_{50}$) is determined from the linear regression of a plot of the logarithm of the concentration versus percent inhibition measured for the different concentrations. Ki's were calculated from IC$_{50}$ based on Cheng-Prusoff equation (Cheng, Y, Prusoff, W H (1973) Biochem Pharmacol 22, 3099-3108): Ki=IC$_{50}$/[1+D/K$_d$] wherein D is the concentration of the radioligand and K$_d$ is the binding constant for the radioligand binding to the receptor under the conditions used in the competition experiment.

The compounds of the present invention exhibit K$_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 1 | 6.5 |
| Example 13 | 11.2 |
| Example 27 | 28.8 |
| Example 31 | 5.6 |
| Example 42 | 6.9 |
| Example 50 | 4.4 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner. MS=mass spectrometry.

EXAMPLES

Example 1

Trans-(4-Cyclobutyl-piperazin-1-yl)-[4-(4-[1,2,4] triazol-1-yl-phenoxy)-cyclohexyl]-methanone a) Step 1: cis-(4-Cyclobutyl-piperazin-1-yl)-(4-hydroxy-cyclohexyl)-methanone (Intermediate 1)

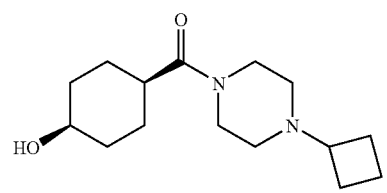

A mixture of 214 mg (1.5 mmol) of cis-4-hydroxycyclohexanecarboxylic acid (commercially available), 316 mg (1.5 mmol) of 1-(2-cyclobutyl)-piperazine dihydrogen chloride (WO 2004101546), 572 mg (1.8 mmol) of TBTU and 751 mg (7.4 mmol) of DIPEA in 5 ml DMF was stirred for 8 h at room temperature. The mixture was diluted with ethyl acetate, washed with water and brine, and evaporated. The residue was purified by column chromatography on silica eluting with CH$_2$Cl$_2$ and methanol=9:1. Evaporation of the combined product fractions yielded 300 mg (76%) of the title compound as light brown oil. MS (m/e): 267.1 (MH$^+$).

b) Step 2: trans-(4-Cyclobutyl-piperazin-1-yl)-[4-(4-[1,2,4]triazol-1-yl-phenoxy)-cyclohexyl]-methanone To a mixture of 200 mg (0.75 mmol) of cis-(4-cyclobutyl-piperazin-1-yl)-(4-hydroxy-cyclohexyl)-methanone, 133 mg (0.83 mmol) of 4-(1,2,4-triazole-1-yl)phenol, 241 mg (0.92 mmol) of triphenylphosphine in 1.5 ml of THF, a mixture of 212 mg (0.92 mmol) of di-tert-butyl azodicarboxylate in 1.5 ml of THF was added dropwise at 0° C., and stirred for 72 h at room temperature. After evaporation, the residue was purified by column chromatography on silica gel elating with CH$_2$Cl$_2$ and methanol=from 99:1 to 9:1. After that, the residue was purified by column chromatography on NH$_2$-coating silica gel eluting % with CH$_2$Cl$_2$ and ethyl acetate=from 100:0 to 99:2. The combined product fractions were evaporated to dryness to yield 35 mg (11%) of the title compound. MS (m/e): 410.3 (MH$^+$).

According to the procedure described for example 1, further piperazinyl-carbonyl-cyclohexyl derivatives had been synthesized from their respective starting materials mentioned in table 1. Table 1 comprises example 2 and example 3.

acetate, washed with water and brine, and evaporated. The residue was purified by column chromatography on NH$_2$-silica gel eluting with CH$_2$Cl$_2$ and methanol=from 100:0 to 98:2. Evaporation of the combined product fractions yielded 600 mg (65%) of the title compound as light brown oil. MS (m/e): 267.1 (MH$^+$).

b) Step 2: cis-[4-(6-Chloro-pyridin-3-yloxy)-cyclohexyl]-(4-cyclobutyl-piperazin-1-yl)-methanone According to the procedure described for example 1, the title compound had been synthesized from trans-(4-cyclobutyl-piperazin-1-yl)-(4-hydroxy-cyclohexyl)-methanone and 2-chloro-5-hydroxypyridine. MS (m/e): 378.3 (MH$^+$).

Example 5 cis-[4-(5-Chloro-pyridin-2-yloxy)-cyclohexyl]-(4-cyclobutyl-piperazin-1-yl)-methanone According to the procedure described for example 1, the title compound had been synthesized from trans-(4-cyclobu-

TABLE 1

| Ex. No. | MW | Name | Starting materials | MW found (MH$^+$) |
|---|---|---|---|---|
| 2 | 377.9 | trans-[4-(6-Chloro-pyridin-3-yloxy)-cyclohexyl]-(4-cyclobutyl-piperazin-1-yl)-methanone | cis-(4-cyclobutyl-piperazin-1-yl)-(4-hydroxy-cyclohexyl)-methanone (intermediate 1) and 2-chloro-5-hydroxypyridine (commercially available) | 378.4 |
| 3 | 377.9 | trans-[4-(5-Chloro-pyridin-2-yloxy)-cyclohexyl]-(4-cyclobutyl-piperazin-1-yl)-methanone | cis-(4-cyclobutyl-piperazin-1-yl)-(4-hydroxy-cyclohexyl)-methanone (intermediate 1) and 5-chloro-2-hydroxypyridine (commercially available) | 378.4 |

Example 4 cis-[4-(6-Chloro-pyridin-3-yloxy)-cyclohexyl]-(4-cyclobutyl-piperazin-1-yl)-methanone a) Step 1: trans-(4-Cyclobutyl-piperazin-1-yl)-(4-hydroxy-cyclohexyl)-methanone (Intermediate 2)

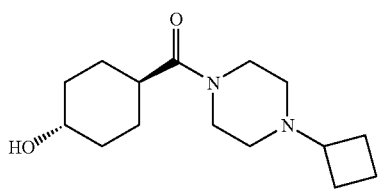

A mixture of 500 mg (3.5 mmol) of cis-4-hydroxycyclohexanecarboxylic acid (commercially available), 739 mg (3.5 mmol) of 1-(2-cyclobutyl)-piperazine dihydrogen chloride (WO 2004101546), 1.23 g (3.8 mmol) of TBTU and 1.40 g (13.8 mmol) of triethylamine in 7 ml DMF was stirred for 12 h at room temperature. The mixture was diluted with ethyl tyl-piperazin-1-yl)-(4-hydroxy-cyclohexyl)-methanone and 5-chloro-2-hydroxypyridine. MS (m/e): 378.3 (MH$^+$).

Example 6

Trans-(4-Isopropyl-piperazin-1-yl)-[4-(4-[1,3,4]oxadiazol-2-yl-phenoxy)-cyclohexyl]-methanone a) Step 1: cis-(4-isopropyl-piperazin-1-yl)-(4-hydroxy-cyclohexyl)-methanone (Intermediate 3)

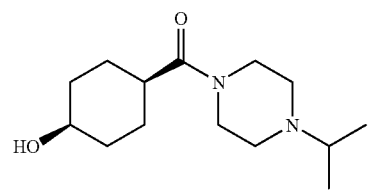

A mixture of 428 mg (3.0 mmol) of cis-4-hydroxycyclohexanecarboxylic acid (commercially available), 318 mg (1.5 mmol) of 1-(isopropyl)-piperazine (commercially available), 1.14 g (3.6 mmol) of TBTU and 900 mg (9 mmol) of triethylamine in 3 ml DMF was stirred for 12 h at room temperature. The mixture was purified by column chromatography on silica eluting with $CH_2Cl_2$ and methanol=9:1. Evaporation of the combined product fractions yielded 460 mg (61%) of the title compound as light brown oil. MS (m/e): 255.2 ($MH^+$).

b) Step 2: trans-(4-isopropyl-piperazin-1-yl)-[4-(4-[1,3,4]oxadiazol-2-yl-phenoxy)-cyclohexyl]-methanone According to the procedure described for example 1, the title compound had been synthesized from cis-(4-isopropyl-piperazin-1-yl)-(4-hydroxy-cyclohexyl)-methanone and 4-(1,3,4-oxadiazole-2-yl)-phenol. MS (m/e): 399.1 ($MH^+$).

According to the procedure described for example 6 further piperazinyl-carbonyl-cyclohexyl derivatives had been synthesized from their respective starting materials mentioned in table 2. Table 2 comprises example 7 to example 9.

Example 11 trans-6-[4-(4-Isopropyl-piperazine-1-carbonyl)-cyclohexyloxy]-nicotinonitrile a) Step 1: trans-(4-isopropyl-piperazin-1-yl)-(4-hydroxy-cyclohexyl)-methanone (Intermediate 4)

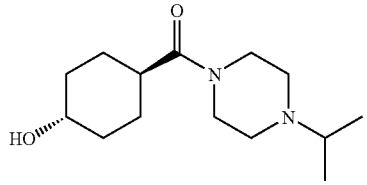

A mixture of 1 g (6.9 mmol) of trans-4-hydroxycyclohexanecarboxylic acid (commercially available), 1.07 mg (8.3 mmol) of 1-(isopropyl)-piperazine (commercially available), 2.67 g (8.3 mmol) of TBTU and 1.54 g (15.2 mmol) of

TABLE 2

| Ex. No. | MW | Name | Starting materials | MW found ($MH^+$) |
|---|---|---|---|---|
| 7 | 414.6 | trans-(4-Isopropyl-piperazin-1-yl)-[4-(4-[1,2,3]thiadiazol-4-yl-phenoxy)-cyclohexyl]-methanone | cis-(4-isopropyl-piperazin-1-yl)-(4-hydroxy-cyclohexyl)-methanone (Intermediate 3) and 4-(1,2,3-thiadiazol-4-yl)phenol (commercially available) | 415.2 |
| 8 | 396.5 | trans-[4-(4-Imidazol-1-yl-phenoxy)-cyclohexyl]-(4-isopropyl-piperazin-1-yl)-methanone | cis-(4-isopropyl-piperazin-1-yl)-(4-hydroxy-cyclohexyl)-methanone (Intermediate 3) and 4-(imidazol-1-yl)phenol (commercially available) | 397.2 |
| 9 | 397.5 | trans-(4-Isopropyl-piperazin-1-yl)-[4-(4-[1,2,4]triazol-1-yl-phenoxy)-cyclohexyl]-methanone | cis-(4-isopropyl-piperazin-1-yl)-(4-hydroxy-cyclohexyl)-methanone (Intermediate 3) and 4-(1,2,4-triazole-1-yl)phenol (commercially available) | 398.2 |

Example 10 trans-6-[4-(4-Cyclobutyl-piperazine-1-carbonyl)-cyclohexyloxy]-nicotinonitrile

To a mixture of 115 mg (0.43 mmol) of trans-(4-Cyclobutyl-piperazin-1-yl)-(4-hydroxy-cyclohexyl)-methanone (Intermediate 3) in 1 ml of N,N-dimethylacetamide (DMA), 19 mg (0.44 mmol) of sodium hydride was added at room temperature and stirred for 30 min. To the mixture, 100 mg (0.72 mmol) of 6-chloronicotinonitrile (commercially available) was added and stirred at 160° C. for 14 h. The mixture was poured into saturated $NaHCO_3$ solution., extracted with AcOEt. The organic layer was washed with water and brine, dried over MgSO4, and evaporated. The residue was purified by column chromatography on silica eluting with $CH_2Cl_2$ and methanol=from 98:2 to 95:5. The combined product fractions were evaporated to dryness to yield 30 mg (11%) of the title compound. MS (m/e): 369.2 ($MH^+$).

triethylamine in 7 ml DMF was stirred for 12 h at room temperature. The mixture was diluted with AcOEt, washed with water and brine, dried over $MgSO_4$, and evaporated. The mixture was purified by column chromatography on $NH_2$-silicagel eluting with $CH_2Cl_2$ and methanol=from 100:0 to 98:2. Evaporation of the combined product fractions yielded 0.9 g (51%) of the title compound as brown oil. MS (m/e): 255.2 ($MH^+$).

b) Step 2 trans-6-[4-(4-Isopropyl-piperazine-1-carbonyl)-cyclohexyloxy]-nicotinonitrile To a mixture of 200 mg (0.79 mmol) of trans-(4-isopropyl-piperazin-1-yl)-(4-hydroxy-cyclohexyl)-methanone (Intermediate 4) in 1 ml of DMA, 42 mg (0.96 mmol) of sodium hydride was added at room temperature and stirred for 30 min. To the mixture, 220 mg (1.59 mmol) of 6-chloronicotinonitrile (commercially available) was added and stirred at 100° C. for 24 h. The mixture was poured into saturated $NaHCO_3$ solution., extracted with AcOEt. The organic layer was washed with water and brine, dried over $MgSO_4$, and evaporated. The residue was purified by column chromatography on silica eluting with $CH_2Cl_2$ and methanol=from 98:2 to 95:5. The combined product fractions were evaporated to dryness to yield 33 mg (6%) of the title compound. MS (m/e): 357.1 ($MH^+$).

According to the procedure described for example 10 and 11, further piperazinyl-carbonyl-cyclohexyl derivatives had been synthesized from their respective starting materials and reaction conditions mentioned in table 3. Table 3 comprises example 12 to example 27. In the last column the solvent employed and the reaction temperature is given.

TABLE 3

| Ex. No. | MW | Name | Starting materials | MW found (MH$^+$) | Solvents/ Temp. (° C.) |
|---|---|---|---|---|---|
| 12 | 409.5 | trans-(4-Isopropyl-piperazin-1-yl)-[4-(5-methanesulfonyl-pyridin-2-yloxy)-cyclohexyl]-methanone | trans-(4-isopropyl-piperazin-1-yl)-(4-hydroxy-cyclohexyl)-methanone (Intermediate 4) and 2-bromo-5-(methylsulfonyl)-pyridine (Bioorg. Med. Chem. Lett (2006), 16(8), 2076) | 410.1 | DMA/ 100° C. |
| 13 | 421.5 | trans-(4-Cyclobutyl-piperazin-1-yl)-[4-(5-methanesulfonyl-pyridin-2-yloxy)-cyclohexyl]-methanone | trans-(4-Cyclobutyl-piperazin-1-yl)-(4-hydroxy-cyclohexyl)-methanone__(Intermediate 3) and 2-bromo-5-(methylsulfonyl)-pyridine | 422.2 | DMA/ 160° C. |
| 14 | 400.5 | trans-6-[4-(4-Cyclobutyl-piperazine-1-carbonyl)-cyclohexyloxy]-N-methyl-nicotinamide | trans-(4-Cyclobutyl-piperazin-1-yl)-(4-hydroxy-cyclohexyl)-methanone__(Intermediate 3) and 6-chloro-N-methyl-3-pyridinecarboxamide (J. Org. Chem. (2006), 71(5), 2000) | 401.2 | DMA/ 160° C. |
| 15 | 414.5 | trans-6-[4-(4-Cyclobutyl-piperazine-1-carbonyl)-cyclohexyloxy]-N,N-dimethyl-nicotinamide | trans-(4-Cyclobutyl-piperazin-1-yl)-(4-hydroxy-cyclohexyl)-methanone__(Intermediate 3) and 6-chloro-N,N-dimethyl-3-pyridinecarboxamide (JP1989102064) | 415.2 | DMA/ 160° C. |
| 16 | 365.9 | trans-[4-(5-Chloro-pyridin-2-yloxy)-cyclohexyl]-(4-isopropyl-piperazin-1-yl)-methanone | trans-(4-isopropyl-piperazin-1-yl)-(4-hydroxy-cyclohexyl)-methanone (Intermediate 4) and 2,5-dichloropyridine (commercially available) | 366.1 | DMA/ 200° C. (microwave reactor) |
| 17 | 458.3 | trans-[4-(6-Iodo-pyridazin-3-yloxy)-cyclohexyl]-(4-isopropyl-piperazin-1-yl)-methanone | trans-(4-isopropyl-piperazin-1-yl)-(4-hydroxy-cyclohexyl)-methanone (Intermediate 4) and 3,6-Diiodopyridazine (J. Med. Chem. (1999), 42, 669) | 459.0 | DMA/ 180° C. (microwave reactor) |
| 18 | 410.3 | trans-[4-(5-Bromo-pyridin-2-yloxy)-cyclohexyl]-(4-isopropyl-piperazin-1-yl)-methanone | trans-(4-isopropyl-piperazin-1-yl)-(4-hydroxy-cyclohexyl)-methanone (Intermediate 4) and 5-bromo-2-nitro-pyridine (commercially available) | 412.1 | DMA/ 200° C. (microwave reactor) |
| 19 | 368.5 | trans-5-[4-(4-Cyclobutyl-piperazine-1-carbonyl)-cyclohexyloxy]-pyridine-2-carbonitrile | trans-(4-Cyclobutyl-piperazin-1-yl)-(4-hydroxy-cyclohexyl)-methanone__(Intermediate 3) and 5-chloro-2-cyanopyridine (commercially available) | 369.1 | DMA/ 160° C. |
| 20 | 422.4 | trans-[4-(6-Bromo-pyridin-3-yloxy)-cyclohexyl]-(4-cyclobutyl-piperazin-1-yl)-methanone | trans-(4-Cyclobutyl-piperazin-1-yl)-(4-hydroxy-cyclohexyl)-methanone__(Intermediate 3) and 2-bromo-5-fluoropyridine (commercially available) | 422.1 | DMA/ 160° C. |

TABLE 3-continued

| Ex. No. | MW | Name | Starting materials | MW found (MH+) | Solvents/ Temp. (° C.) |
|---|---|---|---|---|---|
| 21 | 361.5 | trans-(4-Cyclobutyl-piperazin-1-yl)-[4-(5-fluoro-pyridin-3-yloxy)-cyclohexyl]-methanone | trans-(4-Cyclobutyl-piperazin-1-yl)-(4-hydroxy-cyclohexyl)-methanone (Intermediate 3) and 3,5-difluoropyridine (commercially available) | 362.2 | DMA/ 160° C. |
| 22 | 356.5 | trans-5-[4-(4-Isopropyl-piperazine-1-carbonyl)-cyclohexyloxy]-pyridine-2-carbonitrile | trans-(4-isopropyl-piperazin-1-yl)-(4-hydroxy-cyclohexyl)-methanone (Intermediate 4) and 5-chloro-2-cyanopyridine (commercially available) | 357.2 | DMA/ 200° C. (microwave reactor) |
| 23 | 399.5 | trans-(4-Isopropyl-piperazin-1-yl)-[4-(6-trifluoromethyl-pyridin-3-yloxy)-cyclohexyl]-methanone | trans-(4-isopropyl-piperazin-1-yl)-(4-hydroxy-cyclohexyl)-methanone (Intermediate 4) and 5-bromo-2-(trifluoromethyl)pyridine (commercially available) | 400.2 | DMA/ 200° C. (microwave reactor) |
| 24 | 399.5 | trans-(4-Isopropyl-piperazin-1-yl)-[4-(5-trifluoromethyl-pyridin-2-yloxy)-cyclohexyl]-methanone | trans-(4-isopropyl-piperazin-1-yl)-(4-hydroxy-cyclohexyl)-methanone (Intermediate 4) and 2-bromo-5-(trifluoromethyl)pyridine (commercially available) | 400.3 | DMA/ 190° C. (microwave reactor) |
| 25 | 433.9 | trans-[4-(3-Chloro-5-trifluoromethyl-pyridin-2-yloxy)-cyclohexyl]-(4-isopropyl-piperazin-1-yl)-methanone | trans-(4-isopropyl-piperazin-1-yl)-(4-hydroxy-cyclohexyl)-methanone (Intermediate 4) and 2,3-dichloro-5-(trifluoromethyl)pyridine (commercially available) | 434.2 | DMA/ 190° C. (microwave reactor) |
| 26 | 417.4 | trans-[4-(3-Fluoro-5-trifluoromethyl-pyridin-2-yloxy)-cyclohexyl]-(4-isopropyl-piperazin-1-yl)-methanone | trans-(4-isopropyl-piperazin-1-yl)-(4-hydroxy-cyclohexyl)-methanone (Intermediate 4) and 2,3-dichloro-5-(trifluoromethyl)pyridine (commercially available) | 418.0 | DMA/ 190° C. (microwave reactor) |
| 27 | 394.5 | trans-2-[4-(4-Isopropyl-piperazine-1-carbonyl)-cyclohexyloxy]-thiazole-4-carboxylic acid methylamide | trans-(4-isopropyl-piperazin-1-yl)-(4-hydroxy-cyclohexyl)-methanone (Intermediate 4) and 2-Bromo-thiazole-4-carboxylic acid methylamide | 395.3 | THF:DMA = 1:1/ 100° C. |

Example 28 trans-(4-Isopropyl-piperazin-1-yl)-{4-[4-(5-methyl-[1,3,4]oxadiazol-2-yl)-phenoxy]-cyclohexyl}-methanone a) Step 1: trans-4-[4-(4-Isopropyl-piperazine-1-carbonyl)-cyclohexyloxy]-benzoic acid To a mixture 3.5 g (13.8 mmol) of cis-(4-Isopropyl-piperazin-1-yl)-(4-hydroxycyclohexyl)-methanone, 2.35 g (15.4 mmol) of methyl 4-hydroxybenzoate, 4.47 g (17.0 mmol) of triphenylphosphine in 12 ml of THF, a mixture of 3.88 g (16.9 mmol) of di-tert-butyl azodicarboxylate in 13 ml of THF was added dropwise at 0° C., and stirred for 24 h at room temperature. After evaporation, the residue was purified by column chromatography on silica gel eluting with $CH_2Cl_2$ and methanol=from 98:2 to 9:1. After evaporation of the combined products, the residue was purified by column chromatography on silica gel eluting with $CH_2Cl_2$ and MeOH=from 100:0 to 19:1. The combined product fractions were evaporated to dryness to yield 1.34 g (25%) of trans-4-[4-(4-Isopropyl-piperazine-1-carbonyl)-cyclohexyloxy]-benzoic acid methyl ester. A mixture of 0.6 g (1.5 mmol) of trans-4-[4-(4-Isopropyl-piperazine-1-carbonyl)-cyclohexyloxy]-benzoic acid methyl ester, 42 mg (1.8 mmol) of lithium hydroxide, 6 ml of THF, 3 ml of water, and 1 ml of methanol was stirred at 80° C. for 16 h. After evaporation, the residue was acidified with 2N hydrochloric acid solution and evaporated. The precipitate was washed with water and dried to yield 0.56 g (97%) of the titled compound. MS (m/e): 375 (MH$^+$).

b) Step 2: trans-N'-{4-[4-(4-Isopropyl-piperazine-1-carbonyl)-cyclohexyloxy]-benzoyl}-hydrazinecarboxylic acid tert-butyl ester A mixture of 420 mg (0.93 mmol) of trans-4-[4-(4-Isopropyl-piperazine-1-carbonyl)-cyclohexyloxy]-benzoic acid, 156 mg (1.18 mmol) of tert-butyl carbazate, 272 mg (1.42 mmol) of 1-(3-dimethylaminopropyl)-3-ethylcarbodiimide hydrochloride, 192 mg (1.42 mmol) of 1-hydroxybenzotriazole, and 574 mg (5.67 mmol) of N-methylmorpholine in 10 ml of dichloromethane was stirred for 3 h at room temperature. After evaporation, the mixture was diluted with AcOEt, washed with water and saturated NaHCO$_3$ solution, dried over Na$_2$SO$_4$, and evaporated. The residue was purified by column chromatography on silica eluting with dichloromethane and methanol=from 98:2 to 19:1. The combined product fractions were evaporated to dryness to yield 0.46 g (quant.) of the title compound. MS (m/e): 489.4 (MH$^+$).

c) Step 3: trans-4-[4-(4-Isopropyl-piperazine-1-carbonyl)-cyclohexyloxy]-benzoic acid hydrazide A mixture of 440 mg (0.90 mmol) of trans-N'-{4-[4-(4-Isopropyl-piperazine-1-carbonyl)-cyclohexyloxy]-benzoyl}-hydrazinecarboxylic acid tert-butyl ester, 1.53 ml (6.12 mmol) of 4M hydrochloric acid in 1,4-dioxane solution and 4 ml of methanol was stirred for 4 h at 40° C. The mixture was evaporated to dryness to yield 0.44 g of the title compound. MS (m/e): 389.2 (MH$^+$).

d) Step 4: trans-(4-Isopropyl-piperazin-1-yl)-{4-[4-(5-methyl-[1,3,4]oxadiazol-2-yl)-phenoxy]-cyclohexyl}-methanone A mixture of 100 mg (0.26 mmol) of trans-4-[4-(4-Isopropyl-piperazine-1-carbonyl)-cyclohexyloxy]-benzoic acid hydrazide and 4 ml of trimethyl orthoacetate was stirred for 10 min at 120° C. using microwave reactor. After evaporation, the mixture was diluted with AcOEt, washed with saturated NaHCO$_3$ solution, water and brine, dried over Na$_2$SO$_4$, and evaporated. The residue was purified by column chromatography on silica eluting with dichloromethane and methanol=from 98:2 to 19:1. The combined product fractions were evaporated to dryness to yield 15 mg (14%) of the title compound. MS (m/e): 413.4 (MH$^+$).

Example 29 trans-(4-Cyclobutyl-piperazin-1-yl)-{4-[4-(5-methyl-[1,3,4]oxadiazol-2-yl)-phenoxy]-cyclohexyl}-methanone According to the procedures described for example 28, the titled compound was synthesized from cis-(4-Cyclobutyl-piperazin-1-yl)-(4-hydroxy-cyclohexyl)-methanone as starting material instead of cis-(4-Isopropyl-piperazin-1-yl)-(4-hydroxy-cyclohexyl)-methanone in step 1 of example 28. MS (m/e): 425.3 (MH$^+$).

Example 30 trans-(4-Isopropyl-piperazin-1-yl)-{4-[4-(5-trifluoromethyl-[1,3,4]oxadiazol-2-yl)-phenoxy]-cyclohexyl}-methanone A mixture of 80 mg (0.21 mmol) of trans-4-[4-(4-Isopropyl-piperazine-1-carbonyl)-cyclohexyloxy]-benzoic acid hydrazide, 0.04 ml (0.28 mmol) of trifluoroacetic anhydride, 0.05 ml (0.36 mmol) of triethylamine, and 2 ml of dichloromethane was stirred for 22 hr at room temperature. The mixture was diluted with dichloromethane, washed with saturated NaHCO$_3$ solution, dried over Na$_2$SO$_4$, and evaporated. A mixture of the residue and 2.0 ml (28 mmol) of thionyl chloride was stirred for 18 hr at room temperature. The mixture was diluted with AcOEt, washed with saturated NaHCO$_3$ solution, water and brine, dried over Na$_2$SO$_4$, and evaporated. The residue was purified by column chromatography on silica eluting with dichloromethane and methanol=from 98:2 to 19:1. The combined product fractions were evaporated to dryness to yield 30 mg (31%) of the title compound. MS (m/e): 467.3 (MH$^+$).

Example 31 trans-{4-[4-(5-Isopropyl-[1,3,4]oxadiazol-2-yl)-phenoxy]-cyclohexyl}-(4-isopropyl-piperazin-1-yl)-methanone A mixture of 100 mg (0.25 mmol) of trans-4-[4-(4-Isopropyl-piperazine-1-carbonyl)-cyclohexyloxy]-benzoic acid hydrazide, 0.06 ml (0.57 mmol) of isobutyric acid and 2 ml of phosphorus oxychloride was refluxed for 3 hr. To the mixture, 1N NaOH solution was added. The mixture was extracted with AcOEt, washed with saturated NaHCO$_3$ solution, dried over Na$_2$SO$_4$, and evaporated. The residue was purified by column chromatography on silica eluting with dichloromethane and methanol=from 98:2 to 19:1. The combined product fractions were evaporated to dryness to yield 40 mg (35%) of the title compound. MS (m/e): 441.1 (MH$^+$).

Example 32 trans-{4-[4-(5-Cyclopropyl-[1,3,4]oxadiazol-2-yl)-phenoxy]-cyclohexyl}-(4-isopropyl-piperazin-1-yl)-methanone A mixture of 80 mg (0.21 mmol) of trans-4-[4-(4-Isopropyl-piperazine-1-carbonyl)-cyclohexyloxy]-benzoic acid hydrazide, 0.02 ml (0.26 mmol) of cyclopropanecarboxylic acid and 2 ml of phosphorus oxychloride was refluxed for 2 hr. To the mixture, 1N NaOH solution was added. The mixture was extracted with AcOEt, washed with saturated NaHCO$_3$ solution, dried over Na$_2$SO$_4$, and evaporated. The residue was purified by column chromatography on silica eluting with dichloromethane and methanol=from 98:2 to 19:1. The combined product fractions were evaporated to dryness to yield 56 mg (56%) of the title compound. MS (m/e): 439.4 (MH$^+$).

Example 33 trans-{4-[4-(5-tert-Butyl-[1,3,4]oxadiazol-2-yl)-phenoxy]-cyclohexyl}-(4-isopropyl-piperazin-1-yl)-methanone A mixture of 60 mg (0.15 mmol) of trans-4-[4-(4-Isopropyl-piperazine-1-carbonyl)-cyclohexyloxy]-benzoic acid hydrazide, 0.02 ml (0.2 mmol) of pivalic acid and 2 ml of phosphorus oxychloride was refluxed for 2 hr. To the mixture, 1N NaOH solution was added. The mixture was extracted with AcOEt, washed with saturated NaHCO$_3$ solution, dried over Na$_2$SO$_4$, and evaporated. The residue was purified by column chromatography on silica eluting with dichloromethane and methanol=from 98:2 to 19:1. The combined product fractions were evaporated to dryness to yield 25 mg (36%) of the title compound. MS (m/e): 455.4 (MH$^+$).

Example 34 trans-(4-Isopropyl-piperazin-1-yl)-{4-[4-(5-methyl-[1,2,4]oxadiazol-3-yl)-phenoxy]-cyclohexyl}-methanone a) Step 1: trans-[4-(4-cyano-phenoxy)-cyclohexyl]-(4-isopropyl-piperazin-1-yl)-methanone To a mixture of 1.0 g (3.93 mmol) of cis-(4-isopropyl-piperazin-1-yl)-(4-hydroxy-cyclohexyl)-methanone, 0.515 g (4.3 mmol) of 4-cyanophenol, 1.28 g (4.88 mmol) of triphenylphisphine in 6 ml THF, 1.11 g (4.82 mmol) of di-tert-butyl azodicarboxylate in 6 ml of THF was added at 0° C., and stirred for 72 hr at room temperature. After evaporation, the residue was purified by column chromatography on silica gel eluting with cyclohexane and ethyl acetate=from 1:1 to 1:3, then dichloromethane and methanol=19:1. The combined product fractions were evaporated to dryness to yield 0.26 g (19% yields) of the titled compound. MS (m/e): 356.2 (MH$^+$).

b) Step 2: trans-N-Hydroxy-4-[4-(4-isopropyl-piperazine-1-carbonyl)-cyclohexyloxy]-benzamidine A mixture of 0.15 g (0.42 mmol) of trans-[4-(4-cyano-phenoxy)-cyclohexyl]-(4-isopropyl-piperazin-1-yl)-methanone, 0.118 g (1.69 mmol) of hydroxylamine hydrochloride, 0.24 ml (1.73 mmol) of triethylamine in 3 ml ethanol was refluxed for 1 hr. The mixture was evaporated to dryness to yield 0.34 g (84% yields, about 40% purity) of the titled compound. MS (m/e): 389.3 (MH$^+$).

c) Step 3: trans-(4-Isopropyl-piperazin-1-yl)-{4-[4-(5-methyl-[1,2,4]oxadiazol-3-yl)-phenoxy]-cyclohexyl}-methanone To a mixture of 0.1 g (0.26 mmol) of trans-N-Hydroxy-4-[4-(4-isopropyl-piperazine-1-carbonyl)-cyclohexyloxy]-benzamidine and 0.24 g of molecular sieves 4A in 3 ml THF, 17 mg (0.39 mmol, 55% purity) of sodium hydride was added and the mixture was stirred at 60° C. for 45 min. After cooling down, 0.1 ml (1.45 mmol) of methyl acetate was dropwised to the mixture and the mixture was refluxed for 5 hr. After that, 56 mg (1.28 mmol, 55% purity) of sodium hydride and 1 ml (14.5 mmol) of methyl acetate were added to the mixture. The mixture was refluxed for 16 hr. The mixture was filtered and the filtrate was evaporated. The residue was purified by column chromatography on silica gel eluting with dichloromethane and methanol=from 98:2 to 19:1, after that, purified with cyclohexane and ethyl acetate=from 3:1 to 2:1. The combined product fractions were evaporated to dryness to yield 0.022 g (20% yields) of the titled compound. MS (m/e): 413.4 (MH$^+$).

Example 35 trans-(4-Cyclobutyl-piperazin-1-yl)-{4-[4-(5-methyl-[1,2,4]oxadiazol-3-yl)-phenoxy]-cyclohexyl}-methanone According to the procedures described for example 34, the titled compound was synthesized from cis-(4-Cyclobutyl-piperazin-1-yl)-(4-hydroxy-cyclohexyl)-methanone as starting material instead of cis-(4-Isopropyl-piperazin-1-yl)-(4-hydroxy-cyclohexyl)-methanone in step 1 of example 34. MS (m/e): 425.2 (MH$^+$).

Example 36 trans-(4-Isopropyl-piperazin-1-yl)-{4-[4-(3-methyl-[1,2,4]oxadiazol-5-yl)-phenoxy]-cyclohexyl}-methanone A mixture of 0.1 g (0.22 mmol) of trans-4-[4-(4-Isopropyl-piperazine-1-carbonyl)-cyclohexyloxy]-benzoic acid and 59 mg (0.36 mmol) of 1,1'-carbonyl-diimidazole in 2 ml THF was refluxed for 16 hr. After cooling down, 79 mg (1.1 mmol) of acetamide oxime was added and the mixture was refluxed for 48 hr. To the mixture, 29 mg (0.66 mmol, 55% purity) of sodium hydride was added and the mixture was refluxed for 16 hr. The mixture was evaporated. The mixture was diluted with AcOEt, washed with saturated NaHCO$_3$ solution, dried over Na$_2$SO$_4$, and evaporated. The residue was purified by column chromatography on silica eluting with dichloromethane and methanol=from 98:2 to 9:1. The combined product fractions were evaporated to dryness to yield 40 mg (44%) of the title compound. MS (m/e): 413.2 (MH$^+$).

Example 37 trans-1-{4-[4-(4-Isopropyl-piperazine-1-carbonyl)-cyclohexyloxy]-phenyl}-piperidin-2-one To a mixture of 1.04 g (4.09 mmol) of cis-(4-isopropyl-piperazin-1-yl)-(4-hydroxy-cyclohexyl)-methanone, 1.50 g (6.82 mmol) of 4-iodephenol, 1.25 g (4.77 mmol) of triphenylphisphine in 5 ml THF, 1.1 g (4.78 mmol) of di-tert-butyl azodicarboxylate was added at 0° C., and stirred for 12 h at room temperature. After evaporation, the residue was purified by column chromatography on silica gel eluting with cyclohexane and ethyl acetate=from 100:0 to 2:1. The combined product fractions were evaporated to dryness to yield 0.67 g (14% yields, about 67% purity) of [4-(4-iodo-phenoxy)-cyclohexyl]-(4-isopropyl-piperazin-1-yl)-methanone. A mixture 100 mg (0.15 mmol) of [4-(4-iodo-phenoxy)-cyclohexyl]-(4-isopropyl-piperazin-1-yl)-methanone, 87 mg (0.88 mmol) of 2-piperidone, 41 mg (0.3 mmol) of potassium carbonate and 37 mg (0.58 mmol) of copper was stirred at 175 degree for 6 hr. The mixture was diluted with AcOEt, filtered through celite. The filtrate was washed with saturated NaHCO3 solution and brine, dried over MgSO4, and evaporated. The residue was purified by column chromatography on silica eluting with cyclohexane and ethyl acetate=from 100:0 to 1:3. The combined product fractions were evaporated to dryness to yield 30 mg (32%) of the title compound. MS (m/e): 428.3 (MH$^+$).

Example 38 trans-1-{4-[4-(4-Cyclobutyl-piperazine-1-carbonyl)-cyclohexyloxy]-phenyl}-pyrrolidin-2-one To a mixture of 0.87 g (3.27 mmol) of cis-(4-cyclobutyl-piperazin-1-yl)-(4-hydroxy-cyclohexyl)-methanone, 0.80 g (3.64 mmol) of 4-iodephenol, 1.05 g (4.00 mmol) of triphenylphisphine in 20 ml THF, 0.92 g (4.00 mmol) of di-tert-butyl azodicarboxylate was added at 0° C., and stirred for 12 h at room temperature. After evaporation, the residue was purified by column chromatography on silica gel eluting with cyclohexane and ethyl acetate=from 100:0 to 2:1. The combined product fractions were evaporated to dryness to yield 0.54 g (21% yields, about 65% purity) of [4-(4-iodo-phenoxy)-cyclohexyl]-(4-cyclobutyl-piperazin-1-yl)-methanone. A mixture 100 mg of [4-(4-iodo-phenoxy)-cyclohexyl]-(4-cyclobutyl-piperazin-1-yl)-methanone, 142 mg (1.67 mmol) of 2-piperidone, 77 mg (0.56 mmol) of potassium carbonate and 37 mg (1.12 mmol) of copper was stirred at 175 degree for 6 hr. The mixture was diluted with AcOEt, filtered through celite. The filtrate was evaporated. The mixture was purified with preparative HPLC ($CH_3CN$: 0.05% HCOOH-water, Zorbax Comb Ht 20*50 mm, 5 micron). The combined product fractions were evaporated. The residue was solved with saturated $NaHCO_3$, extracted with AcOEt, washed with brine, dried over $MgSO_4$, and evaporated to dryness to yield 31 mg (52%) of the title compound. MS (m/e): 426.2 ($MH^+$).

According to the procedure described for example 37 and 38, further piperazinyl-carbonyl-cyclohexyl derivatives had been synthesized from their respective starting materials and reaction conditions mentioned in table 4. Table 4 comprises example 39 to example 46.

TABLE 4

| Ex. No. | MW | Name | Starting materials | MW found ($MH^+$) |
|---|---|---|---|---|
| 39 | 427.5 | trans-3-{4-[4-(4-Cyclobutyl-piperazine-1-carbonyl)-cyclohexyloxy]-phenyl}-oxazolidin-2-one | trans-[4-(4-iodo-phenoxy)-cyclohexyl]-(4-cyclobutyl-piperazin-1-yl)-methanone and 2-oxazolidone (commercially available) | 428.2 |
| 40 | 415.5 | trans-3-{4-[4-(4-Isopropyl-piperazine-1-carbonyl)-cyclohexyloxy]-phenyl}-oxazolidin-2-one | trans-[4-(4-iodo-phenoxy)-cyclohexyl]-(4-isopropyl-piperazin-1-yl)-methanone and 2-oxazolidone (commercially available) | 416.2 |
| 41 | 429.5 | trans-4-{4-[4-(4-Isopropyl-piperazine-1-carbonyl)-cyclohexyloxy]-phenyl}-morpholin-3-one | trans-[4-(4-iodo-phenoxy)-cyclohexyl]-(4-isopropyl-piperazin-1-yl)-methanone and morpholin-3-one (commercially available) | 430.2 |
| 42 | 441.6 | trans-4-{4-[4-(4-Cyclobutyl-piperazine-1-carbonyl)-cyclohexyloxy]-phenyl}-morpholin-3-one | trans-[4-(4-iodo-phenoxy)-cyclohexyl]-(4-cyclobutyl-piperazin-1-yl)-methanone and morpholin-3-one (commercially available) | 442.2 |
| 43 | 428.6 | trans-1-{4-[4-(4-Isopropyl-piperazine-1-carbonyl)-cyclohexyloxy]-phenyl}-3-methyl-imidazolidin-2-one | trans-[4-(4-iodo-phenoxy)-cyclohexyl]-(4-isopropyl-piperazin-1-yl)-methanone and 1-methyl-2-imidazolidinone (commercially available) | 429.2 |
| 44 | 413.6 | trans-1-{4-[4-(4-Isopropyl-piperazine-1-carbonyl)-cyclohexyloxy]-phenyl}-pyrrolidin-2-one | trans-[4-(4-iodo-phenoxy)-cyclohexyl]-(4-isopropyl-piperazin-1-yl)-methanone and 2-pyrrolidinone (commercially available) | 414.2 |
| 45 | 414.5 | trans-1-{6-[4-(4-Isopropyl-piperazine-1-carbonyl)-cyclohexyloxy]-pyridin-3-yl}-pyrrolidin-2-one | trans-[4-(5-Chloro-pyridin-2-yloxy)-cyclohexyl]-(4-isopropyl-piperazin-1-yl) methanone and 2-pyrrolidinone (commercially available) | 415.2 |
| 46 | 415.5 | trans-[4-(5-Chloro-pyridin-2-yloxy)-cyclohexyl]-(4-isopropyl-piperazin-1-yl)-methanone | trans-[4-(6-Iodo-pyridazin-3-yloxy)-cyclohexyl]-(4-isopropyl-piperazin-1-yl)-methanone and 2-pyrrolidinone (commercially available) | 416.1 |

Example 47 trans-1-(4-Isopropyl-piperazin-1-yl)-[4-(4-thiazol-2-yl-phenoxy)-cyclohexyl]-methanone To a mixture of 1.04 g (4.09 mmol) of cis-(4-isopropyl-piperazin-1-yl)-(4-hydroxy-cyclohexyl)-methanone, 1.50 g (6.82 mmol) of 4-iodephenol, 1.25 g (4.77 mmol) of triphenylphisphine in 5 ml THF, 1.1 g (4.78 mmol) of di-tert-butyl azodicarboxylate was added at 0° C., and stirred for 12 h at room temperature. After evaporation, the residue was purified by column chromatography on silica gel eluting with cyclohexane and ethyl acetate=from 100:0 to 2:1. The combined product fractions were evaporated to dryness to yield 0.67 g (14% yields, about 67% purity) of [4-(4-iodo-phenoxy)-cyclohexyl]-(4-isopropyl-piperazin-1-yl)-methanone. A mixture 100 mg (0.15 mmol) of [4-(4-iodo-phenoxy)-cyclohexyl]-(4-isopropyl-piperazin-1-yl)-methanone, 88 mg (0.24 mmol) of 2-tributylstannylthiazole, 15 mg (0.02 mmol) of bis(triphenylphosphine) palladium(II) dichloride and 2 ml of THF was refluxed for 8 hr under Ar. The mixture was evaporated. The residue was purified by column chromatography on silica eluting with cyclohexane and ethyl acetate=from 100:0 to 2:1. The combined product fractions were evaporated to dryness to yield 33 mg (36%) of the title compound. MS (m/e): 414.2 (MH$^+$).

According to the procedure described for example 47, further piperazinyl-carbonyl-cyclohexyl derivatives had been synthesized from their respective starting materials and reaction conditions mentioned in table 5. Table 5 comprises example 48 to example 52.

Example 53 trans-{4-[5-(3,4-Difluoro-phenyl)-pyridin-2-yloxy]-cyclohexyl}-(4-isopropyl-piperazin-1-yl)-methanone A mixture of 120 mg (0.29 mmol) of [4-(5-bromo-pyridin-2-yloxy)-cyclohexyl]-(4-isopropyl-piperazin-1-yl)-methanone, 69 mg (0.44 mmol) of 3,4-difluorophenylboronic acid, 34 mg (0.03 mmol) of tetrakis(triphenylphosphine)palladium, and 93 mg (0.88 mmol) of sodium carbonate, 1.5 ml of toluene and 0.5 ml of water was refluxed for 5 hr under Ar. The mixture was diluted with AcOEt, washed with saturated NaHCO$_3$ solution and brine, dried over MgSO$_4$, and evaporated. The residue was purified by column chromatography on silica eluting with cyclohexane and ethyl acetate=from 100:0 to 4:1. The combined product fractions were evaporated to dryness to yield 22 mg (17%) of the title compound. MS (m/e): 444.2 (MH$^+$).

Example 54 trans-(4-Isopropyl-piperazin-1-yl)-{4-[4-(1H-tetrazol-5-yl)-phenoxy]-cyclohexyl}-methanone A mixture of 60 mg (0.17 mmol) of [4-(4-cyano-phenoxy)-cyclohexyl]-(4-isopropyl-piperazin-1-yl)-methanone, 39 mg (0.34 mmol) of 2-trimethylsilyl azide, 6 mg (0.03 mmol) of dibutyltin oxide and 2 ml of toluene was refluxed for 14 hr. The mixture was evaporated. The residue was purified by preparative TLC eluting with dichloromethane and metha-

TABLE 5

| Ex. No. | MW | Name | Starting materials | MW found (MH+) |
|---|---|---|---|---|
| 48 | 407.6 | trans-(4-Isopropyl-piperazin-1-yl)-[4-(4-pyridin-2-yl-phenoxy)-cyclohexyl]-methanone | trans-[4-(4-iodo-phenoxy)-cyclohexyl]-(4-isopropyl-piperazin-1-yl)-methanone and 2-tributylstannylpyridine (commercially available) | 408.1 |
| 49 | 407.6 | trans-(4-Isopropyl-piperazin-1-yl)-[4-(4-pyridin-3-yl-phenoxy)-cyclohexyl]-methanone | trans-[4-(4-iodo-phenoxy)-cyclohexyl]-(4-isopropyl-piperazin-1-yl)-methanone and 3-tributylstannylpyridine (commercially available) | 408.1 |
| 50 | 407.6 | trans-(4-Isopropyl-piperazin-1-yl)-[4-(4-pyridin-4-yl-phenoxy)-cyclohexyl]-methanone | trans-[4-(4-iodo-phenoxy)-cyclohexyl]-(4-isopropyl-piperazin-1-yl)-methanone and 4-tributylstannylpyridine (commercially available) | 408.2 |
| 51 | 408.5 | trans-(4-Isopropyl-piperazin-1-yl)-[4-(4-pyrazin-2-yl-phenoxy)-cyclohexyl]-methanone | trans-[4-(4-iodo-phenoxy)-cyclohexyl]-(4-isopropyl-piperazin-1-yl)-methanone and 2-tributylstannylpyrazine (commercially available) | 409.1 |
| 52 | 397.5 | trans-(4-Isopropyl-piperazin-1-yl)-[4-(4-oxazol-2-yl-phenoxy)-cyclohexyl]-methanone | trans-[4-(4-iodo-phenoxy)-cyclohexyl]-(4-isopropyl-piperazin-1-yl)-methanone and 2-(tri-n-butylstannyl)oxazole (commercially available) | 398.1 | nol=4:1. The product fractions were evaporated to dryness to yield 14 mg (20%) of the title compound. MS (m/e): 399.2 (MH+).

Example A

Film coated tablets containing the following ingredients can be manufactured in a conventional manner:

| Ingredients | Per table | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of formula I:

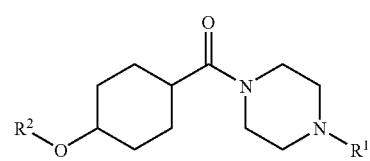

or a pharmaceutically acceptable salt thereof, wherein:
$R^1$ is a $C_1$-$C_8$-alkyl or $C_3$-$C_7$-cycloalkyl; and
$R^2$ is selected from the group consisting of:

(a) phenyl which is substituted by heteroaryl or heterocyclyl, wherein said heteroaryl or heterocyclyl is unsubstituted or substituted with one or two substituents independently selected from the group consisting of:
  (1) $C_1$-$C_8$-alkyl,
  (2) $C_3$-$C_7$-cycloalkyl,
  (3) halogen,
  (4) halogen-$C_1$-$C_8$-alkyl,
  (5) oxo,
  (6) cyano,
  (7) $C_1$-$C_8$-alkoxy,
  (8) halogen-$C_1$-$C_8$-alkoxy, and
  (9) hydroxy-$C_1$-$C_8$-alkyl, and
(b) heteroaryl, wherein the heteroaryl is unsubstituted or substituted with one or two substituents independently selected from the group consisting of:
  (1) $C_1$-$C_8$-alkyl,
  (2) halogen,
  (3) halogen-$C_1$-$C_8$-alkyl,
  (4) cyano,
  (5) $C_1$-$C_8$-alkoxy,
  (6) $C_1$-$C_8$-alkylsulfonyl,
  (7) $C_1$-$C_8$-alkylaminocarbonyl,
  (8) di-$C_1$-$C_8$-alkylaminocarbonyl,
  (9) heterocyclyl which is unsubstituted or substituted with one or two substituents independently selected from the group consisting of $C_1$-$C_8$-alkyl, halogen and oxo, and
  (10) phenyl which is unsubstituted or substituted by one to three substituents independently selected from the group consisting of $C_1$-$C_8$-alkyl, halogen, halogen-$C_1$-$C_8$-alkyl, cyano, and $C_1$-$C_8$-alkoxy.

2. A compound of claim 1, wherein $R^1$ is a $C_1$-$C_8$-alkyl.

3. A compound of claim 1, wherein $R^1$ is isopropyl.

4. A compound of claim 1, wherein $R^1$ is a $C_3$-$C_7$-cycloalkyl.

5. A compound of claim 1, wherein $R^1$ is cyclobutyl.

6. A compound of claim 1, wherein $R^2$ is phenyl substituted by a heteroaryl or heterocyclyl, wherein said heteroaryl or heterocyclyl is unsubstituted or substituted with one or two substituents independently selected from the group consisting of $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy, and hydroxy-$C_1$-$C_8$-alkyl.

7. A compound of claim 1, wherein $R^2$ is phenyl substituted by a heteroaryl or heterocyclyl selected from the group consisting of tetrazolyl, triazolyl, oxazolyl, oxadiazolyl, thiazolyl, thiadiazolyl, imidazolyl, pyridinyl, pyrazinyl, piperidinyl, pyrrolidinyl, oxazolidinyl, morpholinyl and imidazolidinyl; wherein said heteroaryl or heterocyclyl is unsubstituted or substituted with one or two substituents independently selected from the group consisting of $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy, and hydroxy-$C_1$-$C_8$-alkyl.

8. A compound of claim 1, wherein $R^2$ is phenyl substituted by a heteroaryl selected from the group consisting of tetrazolyl, triazolyl, oxazolyl, oxadiazolyl, thiazolyl, thiadiazolyl, imidazolyl, pyridinyl and pyrazinyl; wherein said heteroaryl is unsubstituted or substituted with one or two substituents independently selected from the group consisting of $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy, and hydroxy-$C_1$-$C_8$-alkyl.

9. A compound of claim 1, wherein $R^2$ is selected from the group consisting of: [1,2,4]triazol-1-yl, [1,3,4]oxadiazol-2-yl, [1,2,3]thiadiazol-4-yl, imidazol-1-yl, [1,2,4]triazol-1-yl, 5-methyl-[1,3,4]oxadiazol-2-yl, 5-trifluoromethyl-[1,3,4]oxadiazol-2-yl, 5-isopropyl-[1,3,4]oxadiazol-2-yl, 5-cyclopropyl-[1,3,4]oxadiazol-2-yl, 5-tert-butyl-[1,3,4]oxadiazol-2-yl, [1,2,4]oxadiazol-3-yl, 5-methyl-[1,2,4]oxadiazol-3-yl, [1,2,4]oxadiazol-5-yl, 3-methyl-[1,2,4]oxadiazol-5-yl, thiazol-2-yl, pyridin-2-yl, pyridin-3-yl, pyridin-4-yl, pyrazin-2-yl, oxazol-2-yl, and tetrazol-5-yl.

10. A compound of claim 1, wherein $R^2$ is phenyl substituted by a heterocyclyl selected from the group consisting of piperidinyl, pyrrolidinyl, oxazolidinyl, morpholinyl and imidazolidinyl; said heterocyclyl is unsubstituted or substituted with one or two substituents independently selected from the group consisting of $C_1$-$C_8$-alkyl, $C_3$-$C_7$-cycloalkyl, halogen, halogen-$C_1$-$C_8$-alkyl, oxo, cyano, $C_1$-$C_8$-alkoxy, halogen-$C_1$-$C_8$-alkoxy and hydroxy-$C_1$-$C_8$-alkyl.

11. A compound of claim 1, wherein $R^2$ is phenyl substituted by a heterocyclyl selected from the group consisting of 2-oxo-piperidin-1-yl, 2-oxo-pyrrolidin-1-yl, 2-oxo-oxazolidin-3-yl, 3-oxo-morpholin-4-yl, and 3-methyl-2-oxo-imidazolidin-1-yl.

12. A compound of claim 1, wherein $R^2$ is heteroaryl which is unsubstituted or substituted with one or two substituents independently selected from the group consisting of: $C_1$-$C_8$-alkyl; halogen; halogen-$C_1$-$C_8$-alkyl; cyano; $C_1$-$C_8$-alkoxy; $C_1$-$C_8$-alkylsulfonyl; $C_1$-$C_8$-alkylaminocarbonyl; di-$C_1$-$C_8$-alkylaminocarbonyl; heterocyclyl which is unsubstituted or substituted with one or two substituents independently selected from the group consisting of $C_1$-$C_8$-alkyl, halogen and oxo; and phenyl which is unsubstituted or substituted by one to three substituents selected from the group consisting of $C_1$-$C_8$-alkyl, halogen, halogen-$C_1$-$C_8$-alkyl, cyano, and $C_1$-$C_8$-alkoxy.

13. A compound of claim 1, wherein $R^2$ is heteroaryl selected from the group consisting of pyridyl, pyridazinyl and thiazolyl; wherein said heteroaryl is unsubstituted or substituted with one or two substitutents independently selected from the group consisting of $C_1$-$C_8$-alkyl; halogen; halogen-$C_1$-$C_8$-alkyl; cyano; $C_1$-$C_8$-alkoxy; $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two substituents independently selected from the group consisting of $C_1$-$C_8$-alkyl, halogen and oxo; and phenyl which is unsubstituted or substituted by one to three substituents selected from the group consisting of $C_1$-$C_8$-alkyl, halogen, halogen-$C_1$-$C_8$-alkyl, cyano, and $C_1$-$C_8$-alkoxy.

14. A compound of claim 1, wherein $R^2$ is pyridyl or pyridazinyl; wherein said pyridyl or pyridazinyl is unsubstituted or substituted with one or two substituents independently selected from the group consisting of $C_1$-$C_8$-alkyl; halogen; halogen-$C_1$-$C_8$-alkyl; cyano; $C_1$-$C_8$-alkoxy, $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two substituents independently selected from the group consisting of $C_1$-$C_8$-alkyl, halogen and oxo; and phenyl which is unsubstituted or substituted by one to three substituents independently selected from the group consisting of $C_1$-$C_8$-alkyl, halogen, halogen-$C_1$-$C_8$-alkyl, cyano, and $C_1$-$C_8$-alkoxy.

15. A compound of claim 1, wherein $R^2$ is thiazolyl, said thiazolyl being unsubstituted or substituted with one or two substituents independently selected from the group consisting of $C_1$-$C_8$-alkyl; halogen; halogen-$C_1$-$C_8$-alkyl; cyano; $C_1$-$C_8$-alkoxy, $C_1$-$C_8$-alkylsulfonyl; $C_1$-$C_8$-alkylaminocarbonyl; di-$C_1$-$C_8$-alkylamino-carbonyl; heterocyclyl which is unsubstituted or substituted with one or two substituents independently selected from the group consisting of $C_1$-$C_8$- alkyl, halogen and oxo; and phenyl which is unsubstituted or substituted by one to three substituents independently selected from the group consisting of $C_1$-$C_8$-alkyl, halogen, halogen-$C_1$-$C_8$-alkyl, cyano, and $C_1$-$C_8$-alkoxy.

16. A compound of claim 1, wherein $R^2$ is selected from the group consisting of: 6-chloro-pyridin-3-yl, 6-bromo-pyridin-3-yl, 6-cyano-pyridin-3-yl, 6-trifluoromethyl-pyridin-3-yl, 5-fluoro-pyridin-3-yl, 5-bromo-pyridin-2-yl, 5-chloro-pyridin-2-yl, 5-trifluoromethyl-pyridin-2-yl, 3-chloro-5-trifluoromethyl-pyridin-2-yl, 3-fluoro-5-trifluormethyl-pyridin-2-yl, 5-cyano-pyridin-2-yl, 5-methylsulfonyl-pyridin-2-yl, 5-methylaminocarbonyl-pyridin-2-yl, 5-dimethylaminocarbonyl-pyridin-2-yl, 5-(2-oxo-pyrrolidin-1-yl)-pyridin-2-yl, 6-iodo-pyridazin-3-yl, and 6-(2-oxo-pyrrolidin-1-yl)-pyridazin-3-yl.

17. A compound of claim 1, wherein $R^2$ and the piperazinyl-carboxy group are in trans-configuration.

18. A compound of claim 1, selected from the group consisting of:
trans-(4-cyclobutyl-piperazin-1-yl)-[4-(4-[1,2,4]triazol-1-yl-phenoxy)-cyclohexyl]-methanone,
trans-[4-(6-chloro-pyridin-3-yloxy)-cyclohexyl]-(4-cyclobutyl-piperazin-1-yl)-methanone,
trans-[4-(5-chloro-pyridin-2-yloxy)-cyclohexyl]-(4-cyclobutyl-piperazin-1-yl)-methanone,
cis-[4-(6-chloro-pyridin-3-yloxy)-cyclohexyl]-(4-cyclobutyl-piperazin-1-yl)-methanone,
cis-[4-(5-chloro-pyridin-2-yloxy)-cyclohexyl]-(4-cyclobutyl-piperazin-1-yl)-methanone,
trans-(4-isopropyl-piperazin-1-yl)-[4-(4-[1,3,4]oxadiazol-2-yl-phenoxy)-cyclohexyl]-methanone,
trans-(4-isopropyl-piperazin-1-yl)-[4-(4-[1,2,3]thiadiazol-4-yl-phenoxy)-cyclohexyl]-methanone,
trans-[4-(4-imidazol-1-yl-phenoxy)-cyclohexyl]-(4-isopropyl-piperazin-1-yl)-methanone,
trans-(4-isopropyl-piperazin-1-yl)-[4-(4-[1,2,4]triazol-1-yl-phenoxy)-cyclohexyl]-methanone,
trans-6-[4-(4-cyclobutyl-piperazine-1-carbonyl)-cyclohexyloxy]-nicotinonitrile,
trans-6-[4-(4-isopropyl-piperazine-1-carbonyl)-cyclohexyloxy]-nicotinonitrile, and any pharmaceutically acceptable salt thereof.

19. A compound of claim 1, selected from the group consisting of:
trans-(4-isopropyl-piperazin-1-yl)-[4-(5-methanesulfonyl-pyridin-2-yloxy)-cyclohexyl]-methanone,
trans-(4-cyclobutyl-piperazin-1-yl)-[4-(5-methanesulfonyl-pyridin-2-yloxy)-cyclohexyl]-methanone,
trans-6-[4-(4-cyclobutyl-piperazine-1-carbonyl)-cyclohexyloxy]-N-methyl-nicotinamide,
trans-6-[4-(4-cyclobutyl-piperazine-1-carbonyl)-cyclohexyloxy]-N,N-dimethyl-nicotinamide,
trans-[4-(5-chloro-pyridin-2-yloxy)-cyclohexyl]-(4-isopropyl-piperazin-1-yl)-methanone,
trans-[4-(6-iodo-pyridazin-3-yloxy)-cyclohexyl]-(4-isopropyl-piperazin-1-yl)-methanone,
trans-[4-(5-bromo-pyridin-2-yloxy)-cyclohexyl]-(4-isopropyl-piperazin-1-yl)-methanone,
trans-5-[4-(4-cyclobutyl-piperazine-1-carbonyl)-cyclohexyloxy]-pyridine-2-carbonitrile,
trans-[4-(6-bromo-pyridin-3-yloxy)-cyclohexyl]-(4-cyclobutyl-piperazin-1-yl)-methanone,
trans-(4-cyclobutyl-piperazin-1-yl)-[4-(5-fluoro-pyridin-3-yloxy)-cyclohexyl]-methanone,
trans-5-[4-(4-isopropyl-piperazine-1-carbonyl)-cyclohexyloxy]-pyridine-2-carbonitrile, and any pharmaceutically acceptable salt thereof.

20. A compound of claim 1, selected from the group consisting of:
trans-(4-isopropyl-piperazin-1-yl)-[4-(6-trifluoromethyl-pyridin-3-yloxy)-cyclohexyl]-methanone,
trans-(4-isopropyl-piperazin-1-yl)-[4-(5-trifluoromethyl-pyridin-2-yloxy)-cyclohexyl]-methanone,
trans-[4-(3-chloro-5-trifluoromethyl-pyridin-2-yloxy)-cyclohexyl]-(4-isopropyl-piperazin-1-yl)-methanone,
trans-[4-(3-fluoro-5-trifluoromethyl-pyridin-2-yloxy)-cyclohexyl]-(4-isopropyl-piperazin-1-yl)-methanone,
trans-2-[4-(4-isopropyl-piperazine-1-carbonyl)-cyclohexyloxy]-thiazole-4-carboxylic acid methylamide,
trans-(4-isopropyl-piperazin-1-yl)-{4-[4-(5-methyl-[1,3,4]oxadiazol-2-yl)-phenoxy]-cyclohexyl}-methanone,
trans-(4-cyclobutyl-piperazin-1-yl)-{4-[4-(5-methyl-[1,3,4]oxadiazol-2-yl)-phenoxy]-cyclohexyl}-methanone,
trans-(4-isopropyl-piperazin-1-yl)-{4-[4-(5-trifluoromethyl-[1,3,4]oxadiazol-2-yl)-phenoxy]-cyclohexyl}-methanone,
trans-{4-[4-(5-isopropyl-[1,3,4]oxadiazol-2-yl)-phenoxy]-cyclohexyl}-(4-isopropyl-piperazin-1-yl)-methanone,
trans-{4-[4-(5-cyclopropyl-[1,3,4]oxadiazol-2-yl)-phenoxy]-cyclohexyl}-(4-isopropyl-piperazin-1-yl)-methanone,
trans-{4-[4-(5-tert-butyl-[1,3,4]oxadiazol-2-yl)-phenoxy]-cyclohexyl}-(4-isopropyl-piperazin-1-yl)-methanone, and any pharmaceutically acceptable salt thereof.

21. A compound of claim 1, selected from the group consisting of:
trans-(4-isopropyl-piperazin-1-yl)-{4-[4-(5-methyl-[1,2,4]oxadiazol-3-yl)-phenoxy]-cyclohexyl}-methanone,
trans-(4-cyclobutyl-piperazin-1-yl)-{4-[4-(5-methyl-[1,2,4]oxadiazol-3-yl)-phenoxy]-cyclohexyl}-methanone,
trans-(4-isopropyl-piperazin-1-yl)-{4-[4-(3-methyl-[1,2,4]oxadiazol-5-yl)-phenoxy]-cyclohexyl}-methanone,
trans-1-{4-[4-(4-isopropyl-piperazine-1-carbonyl)-cyclohexyloxy]-phenyl}-piperidin-2-one,
trans-1-{4-[4-(4-cyclobutyl-piperazine-1-carbonyl)-cyclohexyloxy]-phenyl}-pyrrolidin-2-one,
trans-3-{4-[4-(4-cyclobutyl-piperazine-1-carbonyl)-cyclohexyloxy]-phenyl}-oxazolidin-2-one,
trans-3-{4-[4-(4-isopropyl-piperazine-1-carbonyl)-cyclohexyloxy]-phenyl}-oxazolidin-2-one,
trans-4-{4-[4-(4-isopropyl-piperazine-1-carbonyl)-cyclohexyloxy]-phenyl}-morpholin-3-one,
trans-4-{4-[4-(4-cyclobutyl-piperazine-1-carbonyl)-cyclohexyloxy]-phenyl}-morpholin-3-one,
trans-1-{4-[4-(4-isopropyl-piperazine-1-carbonyl)-cyclohexyloxy]-phenyl}-3-methyl-imidazolidin-2-one,
and any pharmaceutically acceptable salt thereof.

22. A compound of claim 1, selected from the group consisting of:
trans-1-{4-[4-(4-isopropyl-piperazine-1-carbonyl)-cyclohexyloxy]-phenyl}-pyrrolidin-2-one,
trans-1-{6-[4-(4-isopropyl-piperazine-1-carbonyl)-cyclohexyloxy]-pyridin-3-yl}-pyrrolidin-2-one,
trans-1-{6-[4-(4-isopropyl-piperazine-1-carbonyl)-cyclohexyloxy]-pyridazin-3-yl}-pyrrolidin-2-one,
trans-(4-isopropyl-piperazin-1-yl)-[4-(4-thiazol-2-yl-phenoxy)-cyclohexyl]-methanone,
trans-(4-isopropyl-piperazin-1-yl)-[4-(4-pyridin-2-yl-phenoxy)-cyclohexyl]-methanone,
trans-(4-isopropyl-piperazin-1-yl)-[4-(4-pyridin-3-yl-phenoxy)-cyclohexyl]-methanone, trans-(4-isopropyl-piperazin-1-yl)-[4-(4-pyridin-4-yl-phenoxy)-cyclohexyl]-methanone,
trans-(4-isopropyl-piperazin-1-yl)-[4-(4-pyrazin-2-yl-phenoxy)-cyclohexyl]-methanone,
trans-(4-isopropyl-piperazin-1-yl)-[4-(4-oxazol-2-yl-phenoxy)-cyclohexyl]-methanone,
trans-{4-[5-(3,4-difluoro-phenyl)-pyridin-2-yloxy]-cyclohexyl}-(4-isopropyl-piperazin-1-yl)-methanone,
trans-(4-isopropyl-piperazin-1-yl)-{4-[4-(1H-tetrazol-5-yl)-phenoxy]-cyclohexyl}-methanone,
and any pharmaceutically acceptable salt thereof.

23. A compound of claim 1, selected from the group consisting of
trans-(4-cyclobutyl-piperazin-1-yl)-[4-(4-[1,2,4]triazol-1-yl-phenoxy)-cyclohexyl]-methanone,
trans-(4-isopropyl-piperazin-1-yl)-{4-[4-(5-methyl-[1,3,4]oxadiazol-2-yl)-phenoxy]-cyclohexyl}-methanone,
trans-(4-cyclobutyl-piperazin-1-yl)-{4-[4-(5-methyl-[1,3,4]oxadiazol-2-yl)-phenoxy]-cyclohexyl}-methanone,
trans-{4-[4-(5-isopropyl-[1,3,4]oxadiazol-2-yl)-phenoxy]-cyclohexyl}-(4-isopropyl-piperazin-1-yl)-methanone,
trans-{4-[4-(5-cyclopropyl-[1,3,4]oxadiazol-2-yl)-phenoxy]-cyclohexyl}-(4-isopropyl-piperazin-1-yl)-methanone,
trans-{4-[4-(5-tert-butyl-[1,3,4]oxadiazol-2-yl)-phenoxy]-cyclohexyl}-(4-isopropyl-piperazin-1-yl)-methanone,
trans-(4-isopropyl-piperazin-1-yl)-{4-[4-(3-methyl-[1,2,4]oxadiazol-5-yl)-phenoxy]-cyclohexyl}-methanone,
trans-4-{4-[4-(4-cyclobutyl-piperazine-1-carbonyl)-cyclohexyloxy]-phenyl}-morpholin-3-one,
trans-1-{4-[4-(4-isopropyl-piperazine-1-carbonyl)-cyclohexyloxy]-phenyl}-3-methyl-imidazolidin-2-one,
trans-(4-isopropyl-piperazin-1-yl)-[4-(4-thiazol-2-yl-phenoxy)-cyclohexyl]-methanone,
trans-(4-isopropyl-piperazin-1-yl)-[4-(4-pyridin-3-yl-phenoxy)-cyclohexyl]-methanone,
trans-(4-isopropyl-piperazin-1-yl)-[4-(4-pyridin-4-yl-phenoxy)-cyclohexyl]-methanone,
trans-(4-isopropyl-piperazin-1-yl)-[4-(4-pyrazin-2-yl-phenoxy)-cyclohexyl]-methanone, and any pharmaceutically acceptable salt thereof.

24. A pharmaceutical composition comprising a therapeutically effective amount of a compound of claim 1 and a pharmaceutically acceptable carrier.

* * * * *